(12) United States Patent
Alam et al.

(10) Patent No.: US 7,129,329 B1
(45) Date of Patent: Oct. 31, 2006

(54) HEME PROTEINS HEMAT-HS AND HEMAT-BS AND THEIR USE IN MEDICINE AND MICROSENSORS

(75) Inventors: Maqsudul Alam, Honolulu, HI (US); Randy Larsen, Kaneohe, HI (US)

(73) Assignee: University of Hawaii, Honolulu, HI (US)

( * ) Notice: Subject to any disclaimer, the term of this patent is extended or adjusted under 35 U.S.C. 154(b) by 0 days.

(21) Appl. No.: 09/455,978

(22) Filed: Dec. 6, 1999

(51) Int. Cl.
*A61K 35/14* (2006.01)
*A61K 38/16* (2006.01)

(52) U.S. Cl. .......................... 530/385; 436/66; 436/68; 514/832; 530/350; 530/380; 530/400; 930/10; 930/200; 930/300

(58) Field of Classification Search .................. 436/66, 436/68; 514/832; 530/350, 380, 385, 400; 930/10, 200, 300
See application file for complete search history.

(56) References Cited

U.S. PATENT DOCUMENTS 5,635,207 A * 6/1997 Grinstaff et al. ............ 424/450

OTHER PUBLICATIONS

Zhao et al. Double Mutant of Sperm Whale Myoglobin Mimics the Structure and Function of Elephant Myoglobin. J. Biol. Chem (1995) vol. 270, No. 35, pp. 20763-20744.*
Sugimoto et al. Myoglobin Mutants Giving the Largest Geminate Yield in CO Rebinding in the Nanosecond Time Domain. Biophysical J. (Nov. 1998) vol. 75, pp. 2188-2194.*
Gong et al. Structure of a biological oxygen sensor: A new mechanism for heme-driven signal transduction. Proc. Natl. Acad. Sci. (Dec. 1998) vol. 95, pp. 15177-15182.*
Yao and Spudich, Primary Structure of an archaebacterial transducer, a methyl-accepting protein associated with sensory rhodopsin I, (1992) Proc. Natl. Acad. Sci. vol. 89, pp. 11915-11919.*
Yao et al. Identification of Distinct Domains for Signalling and Receptor Interaction of the Sensory Rhodopsin I Transducer, Htr (1994) J. Bacteriol. vol. 176, No. 22, pp. 6931-6935.*
Monson et al. The FixL protein of *Rhibzobium meliloti* can be separated into a heme-binding oxygen-sensing domain and a functional C-terminal domain. (1992) Proc. Natl. Acad. Sci. 89: 4280-4284.*
Poole, "Oxygen Reactions with Bacterial Oxidases and Globins: Binding, Reduction and Regulation," *Antonie van Leeuwenhoek* 65:289-310 (1994).
Membrillo-Hernandez et al., "Bacterial Flavohaemoglobins: A Consensus Sequence and Identification of a Discrete Enterobacterial Group and of Further Bacterial Globins," *FEMS Microbiology Letters* 155:179-184 (1997).
Hou et al., "Myoglobin-Like Aerotaxis Transducers in Archaea and Bacteria," *Nature* 403:540-544 (2000).
EMBL Accession No. P71413, "Transducer HTB Protein," Feb. 1, 1997, XP-002171025.
EMBL Accession No. 007621, "Hypothetical 48.8KDA Protein," Jul. 1, 1997, XP-002171026.

Boyd et al., "Structure of the Serine Chemoreceptor in *Escherichia coli*," *Nature* 301:623-626 (1983).
Bashford et al., "Determinants of a Protein Fold. Unique Features of the Globin Amino Acid Sequences," *J. Mol. Biol.* 196:199-216 (1987).
Studier et al., "Use of T7 RNA Polymerase to Direct Expression of Cloned Genes," *Methods in Enzymology* 185:60-89 (1990).
Ihara et al., "The ATP Synthase of *Halobacterium salinarium* (*halobium*) is an Archaebacterial Type as Revealed from the Amino Acid Sequences of its Two Major Subunits," *Archives of Biochemistry and Biophysics* 286(1):111-116 (1991).
Alam et al., Structural Features of Methyl-Accepting Taxis Proteins Conserved Between Archaebacteria and Eubacteria Revealed by Antigenic Cross-Reaction, *Journal of Bacteriology* 173(18):5837-5842 (1991).
Gilles-Gonzalez et al., "A Haemoprotein with Kinase Activity Encoded by the Oxygen Sensor of *Rhizobium meliloti*," *Nature* 350:170-172 (1991).
Hazelbauer, "Bacterial Chemoreceptors," *Current Opinion in Structural Biology* 2:505-510 (1992).
Vinogradov et al., "Adventitious Variability? The Amino Acid Sequences of Nonvertebrate Globins," *Comp. Biochem. Physiol.* 106B(1):1-26 (1993).
Lois et al., "The Oxygen Sensor FixL of *Rizobium meliloti* is a Membrane Protein Containing Four Possible Transmembrane Segments," *Journal of Bacteriology* 175(4):1103-1109 (1993).
Springer et al., "Mechanisms of Ligand Recognition in Myoglobin," *Chem. Rev.* 94:699-714 (1994).
Gilles-Gonzalez et al., "Heme-Based Sensors, Exemplified by the Kinase FixL, Are a New Class of Heme Protein with Distinctive Ligand Binding and Autoxidation," *Biochemistry* 33:8067-8073 (1994).
Kapp, Alignment of 700 Globin Sequences: Extent of Amino Acid Substitution and its Correlation with Variation in Volume, *Protein Science* 4:2179-2190 (1995).
Wong et al., "Role of Methylation in Aerotaxis in *Bacillus subtilis*," *Journal of Bacteriology* 177(14):3985-3991 (1995).
Lindbeck et al., "Aerotaxis in *Halobacterium salinarium* is Methylation-Dependent," *Microbiology* 141:2945-2953 (1995).
Hill et al., "*Azotobacter vinelandii* NIFL is a Flavoprotein that Modulates Transcriptional Activation of Nitrogen-Fixation Genes via a Redox-Sensitive Switch," *Proc. Natl. Acad. Sci. USA* 93:2143-2148 (1996).

(Continued)

Primary Examiner—Kathleen M. Kerr
Assistant Examiner—Holly Schnizer
(74) Attorney, Agent, or Firm—Nixon Peabody LLP

(57) ABSTRACT

The present invention provides an isolated archael and bacterial heme binding protein which reversibly binds oxygen with a low affinity. The heme binding protein may be utilized as a blood substitute. The invention also provides a method for controlled storage of oxygen by contacting a bacterial heme binding protein with oxygen allowing the protein to bind and store oxygen. The also provides methods to sense gaseous ligands using the heme binding protein. In other embodiments, the invention provides chimeric proteins having a heme-binding domain of an isolated heme binding archael bacterial protein and a heterologous signaling domain.

8 Claims, 9 Drawing Sheets

OTHER PUBLICATIONS

Zhang et al., "Signal Transduction in the Archaeon *Halobacterium salinarium* is Processed Through Three Subfamilies of 13 Soluble and Membrane-Bound Transducer Proteins," *Proc. Natl. Acad. Sci. USA* 93:4649-4654 (1996).

Bibikov et al., "A Signal Transducer for Aerotaxis in *Eschericha coli*," *Journal of Bacteriology* 179(12):4075-4079 (1997).

Rebbapragada et al., "The Aer Protein and the Serine Chemoreceptor Tsr Independently Sense Intracellular Energy Levels and Transduce Oxygen, Redox, and Energy Signals for *Escherichia coli* Behavior," *Proc. Natl. Acad. Sci. USA* 94:10541-10546 (1997).

Kunst et al., "The Complete Genome Sequence of the Gram-Positive Bacterium *Bacillus subtilis*," *Nature* 390:249-256 (1997).

Vagner et al., "A Vector for Systematic Gene Inactivation in *Bacillus subtilis*," *Microbiology* 144:3097-3104 (1998).

Zhulin et al., "Correlation of PAS Domains with Electron Transport-Associated Proteins in Completely Sequenced Microbial Genomes," *Molecular Microbiology* 29:1522-1523 (1998).

Brooun et al., "An Archaeal Aerotaxis Transducer Combines Subunit I Core Structures of Eukaryotic Cytochrome c Oxidase and Eubacterial Methyl-Accepting Chemotaxis Proteins," *Journal of Bacteriology* 180(7):1642-1646 (1998).

Larsen et al., "Spectroscopic Characterization of Two Soluble Transducers from the Archaeon *Halobacterium salinarum*," *Journal of Protein Chemistry* 18(3):269-275 (1999).

Gong et al., "Structure of a Biological Oxygen Sensor: A New Mechanism for Heme-Driven Signal Transduction," *Proc. Natl. Acad. Sci. USA* 95:15177-15182 (1998).

Hardison, "Hemoglobins from Bacteria to Man: Evolution of Different Patterns of Gene Expression," *The Journal of Experimental Biology* 201:1099-1117 (1998).

Hardison, "The Evolution of Hemoglobin," *American Scientist* 87:126-137 (1999).

Taylor et al., "Aerotaxis and Other Energy-Sensing Behavior in Bacteria," *Annu. Rev. Microbiol.* 53:103-128 (1999).

* cited by examiner

```
                                                                    42
                                                                    60
                                                                    61

|-- A HELIX --|  |------ B HELIX ------||C HELIX|
                                                      *
SwMb       VL--------SEGEWQLVLHVWAKVEADVA----GHGQDILIRLFKSHPETLEK
HemAT-Hs   MSNDNDTLVTADVRNGIDGHALADRIGLDE--AELAWRLSFTGDDDTMAATAAEQPLFEAT
HemAT-Bs   LLFKKDRKQETAYFSDSNGQKN-RIQLTNKHADVKKQLKMVRLGDAEDYVLEQLQPLIQEN 92
                                                                    122
                                                                    122

|D HELIX||------ E HELIX ------|                |-F HELIX|
                           ◆                                    LKPLAQS
SwMb       FDRFKHLKTEAEMKASEDLKKHGVTVL--TALGAILKK-KGHHEAE----LKPLAQS
HemAT-Hs   ADALVTDF---YDHLESYERTQDLFANSTKTVEQLLKETQAEYLLGI-GREEYDTEYAAQRARIGKI
HemAT-Bs   IVNLVDAF---YKNLDHESSLMDLI-NDHSSVDRLKQTLKRHIQEMFAGVIDDEFIEKRNIASI 153
                                                                    184
                                                                    175

|------ G HELIX ------|  |------ H HELIX ------|
                *
SwMb       HATKHKIPIKYLEFISEAIIHVLHSRHPGDFGADAQGAMNKALELFRKDIAA--KYKELGYQG
HemAT-Hs   HDVLGLGPDVYLGAYFRYYTGLLDATLADDVVADRGEEAAAAAVDELVARELPMLKLLTFDQQI
HemAT-Bs   HLRJGLLPKWYMGATQELLLSMIDIY-------EASLINQQELKAIKATIKIULNLEQQL

SwMb       SEQ. ID. No. 76
HemAT-Hs   SEQ. ID. No. 77
HemAT-Bs   SEQ. ID. No. 78
```

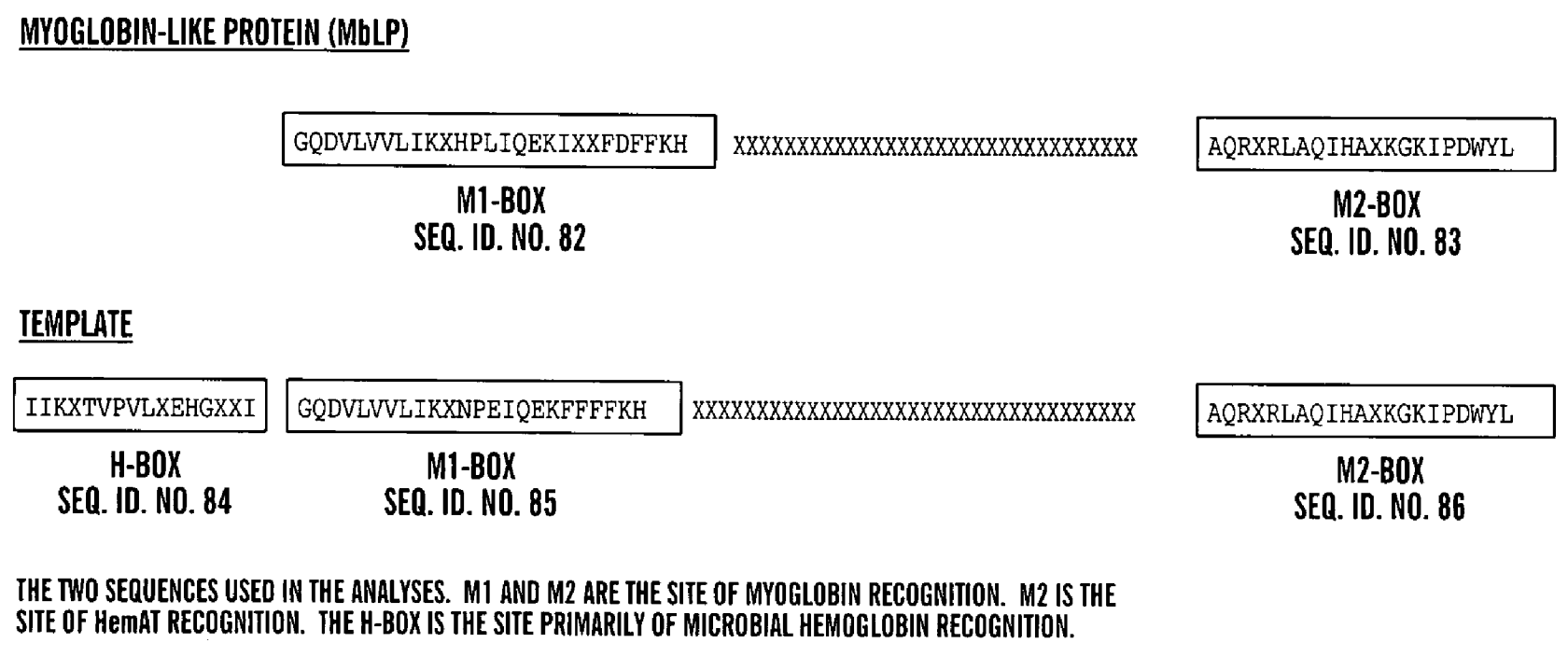

MYOGLOBIN-LIKE PROTEIN (MbLP)

| IIKXTVPVLXEHGXXI | GQDVLVV

H. SALINARUM

B. SUBTILIS

HEME PROTEINS HEMAT-HS AND HEMAT-BS AND THEIR USE IN MEDICINE AND MICROSENSORS

The subject matter of this application was made with support from the United States Government under Grant No. MSB960086 from the National Science Foundation. The United States Government may retain certain rights.

BACKGROUND OF THE INVENTION

Heme proteins such as hemoglobin and myoglobin play an essential role in stabilizing molecular oxygen for transport and storage. The oxygen carrying portion of the red blood cell is hemoglobin, a tetrameric protein molecule composed of two identical alpha globins (alpha 1, alpha 2), two identical beta globins (beta 1, beta 2) and four heme molecules. A heme molecule is incorporated into each of the alpha and beta globins to give alpha and beta subunits. Heme is a macrocyclic organic molecule that contains an iron atom at its center; each heme can combine reversibly with one ligand molecule, for example oxygen. In a hemoglobin tetramer, each alpha subunit is associated with a beta subunit to form two stable alpha/beta dimers, which in turn associate to form the tetramer (a homodimer). The subunits are noncovalently associated through Van der Waals forces, hydrogen bonds and salt bridges. Ligands, particularly oxygen, bind reversibly to the reduced form of the iron (ferrous, $Fe^{2+}$) in the heme. Other ligands which compete with oxygen for the heme group include carbon monoxide and nitric oxide.

It is not always practical to transfuse a patient with donated blood. The well known complications of blood transfusion namely incompatibility reactions, disease transmission, immunosuppression and the storage limitations of erythrocytes points to the need for the development of blood substitutes devoid of these shortcomings. In these situations, use of a red blood cell substitute is necessary. A "blood substitute" is a preparation that does not necessarily replace blood in all of its functions, but an emergency resuscitative fluid that is capable of efficiently transporting oxygen to tissue. This fluid, however, must be free of toxic side-effects, as well as of agents of disease such as bacteria and viruses.

For over 50 years, efforts directed to the development of a blood substitute have focused on hemoglobin (Hb). Hemoglobin (Hgb) is the oxygen-carrying component of blood. Hemoglobin circulates through the bloodstream inside small enucleate cells called erythrocytes (red blood cells). Hemoglobin is a protein constructed from four associated polypeptide chains, and bearing prosthetic groups known as hemes. The erythrocyte helps maintain hemoglobin in its reduced, functional form. The heme iron atom is labile to oxidation, but may be reduced again by one of two enzyme systems within the erythrocyte, the cytochrome b5 and glutathione reduction systems.

Hemoglobin exhibits cooperative binding of oxygen by the four subunits of the hemoglobin molecule (two alpha-globins and two beta-globins in the case of HbA), and this cooperativity greatly facilitates efficient oxygen transport. Cooperativity, achieved by the so-called heme—heme interaction, allows hemoglobin to vary its affinity for oxygen. Hemoglobin reversibly binds up to four moles of oxygen per mole of Hb. At high oxygen concentration, such as that found in the lungs, the oxygen affinity is high and hemoglobin is almost saturated with oxygen. At low oxygen concentration, such as that found in actively respiring tissue, the oxygen affinity is lowered and oxygen is unloaded. The oxygen affinity of hemoglobin is lowered by the presence of 2,3-diphosphoglycerate (2,3-DPG), chloride ions and hydrogen ions. Respiring tissue releases carbon dioxide into the blood and lowers its pH (i.e. increases the hydrogen ion concentration), thereby causing oxygen to dissociate from hemoglobin and allowing it to diffuse into individual cells.

The ability of hemoglobin to alter its oxygen affinity, increasing the efficiency of oxygen transport around the body, is dependent on the presence of the metabolite 2,3-DPG. Inside the erythrocyte 2,3-DPG is present at a concentration nearly as great as that of hemoglobin itself. In the absence of 2,3-DPG "conventional" hemoglobin binds oxygen very tightly and would release little oxygen to respiring tissue.

Aging erythrocytes release small amounts of free hemoglobin into the blood plasma where it is rapidly bound by the scavenging protein haptoglobin. The hemoglobin-haptoglobin complex is removed from the blood and degraded by the spleen and liver.

It is clear from the above considerations that free native hemoglobin A, injected directly into the bloodstream, would not support efficient oxygen transport about the body. The essential allosteric regulator 2,3-DPG is not present in sufficient concentration in the plasma to allow hemoglobin to release much oxygen at venous oxygen tension, and free hemoglobin would be rapidly inactivated as an oxygen carrier by auto-oxidation of the heme iron.

Therefore, a need exists for a substitute other than hemoglobin which can bind and carry oxygen to cells. This substitute may also be used in other applications where hemoglobin is used, including as a biological sensor for oxygen. The present invention provides proteins which meet that need.

SUMMARY OF THE INVENTION

The present invention provides isolated archaeal and bacterial heme binding proteins which reversibly bind oxygen with a low affinity.

The invention also provides a blood substitute containing the bacterial heme binding protein which reversibly binds oxygen with a low affinity.

Another embodiment of the invention is a method for controlled storage of oxygen. A bacterial heme binding protein which reversibly binds oxygen with a low affinity is contacted with oxygen allowing the protein to bind and store oxygen. The invention also provides a method of sensing gaseous ligands. A heme binding bacterial protein is exposed to a test sample and a change in the conformation of the protein is measured.

Yet another embodiment of the invention is a chimeric protein having a heme-binding domain and a heterologous signaling domain.

The invention further provides an isolated nucleic acid molecule which encodes a heme binding bacterial protein that reversibly binds oxygen with a low affinity.

BRIEF DESCRIPTION OF THE DRAWINGS

FIG. 1 shows the conserved sequences within HemAT-Hs, HemAT-Bs, and sperm-whale myoglobin (SWMb). Black boxes indicate positions at which the residues are identical, and gray boxes highlight residues that are similar. Sequences were aligned using the Clustal program of the MegAlign/DNASTAR package. A) Alignment of the amino-terminal domain of HemAT-Hs, HemAT-Bs, and SWMb. Helical regions in SWMb (helices A–H) (B. C. Clothia, et al., *J. Mol.*

*Biol.* 196:199 (1987); S. N. Vinogradov et al., *Comp. Biochem. Physiol.* 106B:1 (1993), which are hereby incorporated by reference) are delineated by dotted arrows. Pro (P), Phe (F), and His (H) residues in SWMb that are highly conserved among all globins are marked with asterisks. B) Alignment of the carboxyl-terminal domains of HemAT-Hs, HemAT-Bs, and Tsr (B. K. Kendall, et al., *Nature* 301:623 (1983); G. L. Hazelbauer, *Curr. Opin. Struct. Biol.,* 2:505 (1992), which are hereby incorporated by reference).

Figure 2A:
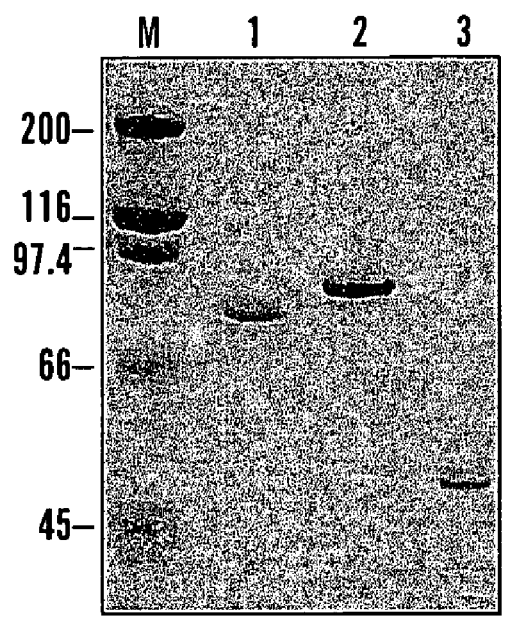
Figure 2B:
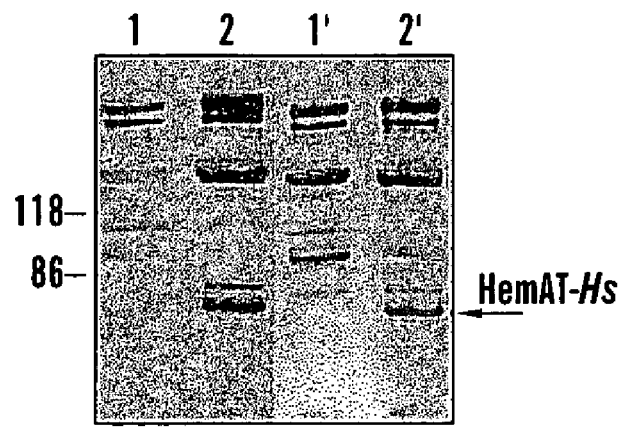

FIG. 2 is a characterization of HemAT proteins. FIG. 2A shows the purified HemAT-Hs and HemAT-Bs in 10% SDS-PAGE. Approximately 5 μg of purified protein were loaded in each lane for separation during SDS-PAGE in 10% acrylamide (M. Alam et al., *J. Bacteriol.,* 173:5837 (1991), which is hereby incorporated by reference). Lane 1, HemAT-Hs; lane 2, HemAT$_{6xHis}$-Hs; and lane 3, HemAT-Bs. The MW markers (kDa) are shown at the left. FIG. 2B is a fluorograph and immunoblot of HemAT-Hs. Radiolabeling and immunoblotting were performed as previously described (M. Alam et al., *J. Bacteriol.,* 173:5837 (1991), which is hereby incorporated by reference). Lane 1, fluorograph of proteins from the ΔhemAT-Hs; lane 2, fluorograph of proteins from the ΔhemAT-Hs/hemAT-Hs++ strain (A. Brooun, Ph.D thesis. University of Hawaii, Hawaii (1997), which is hereby incorporated by reference). NdeI and XbaI restriction sites were used to clone the hemAT-Hs gene into the shuttle vector pKJ427. Primers introducing flanking NdeI and XbaI restriction sites were used for PCR amplification. The PCR product was initially cloned into the pCRR-Blunt II TOPO cloning vector and later subcloned into plasmid pKJ427 after digestion with NdeI and XbaI. The resulting plasmid was introduced into the ΔhemAT-Hs strain. Lane 1: immunoblot of ΔhemAT-Hs strain; and lane 2: immunoblot of ΔhemAT-Hs/hemAT-Hs++ strain using anti-transducer peptide antibody (W. Zhang et al., *Proc. Natl. Acad. Sci. U.S.A.* 93:4649 (1996), which is hereby incorporated by reference). Bars indicate the positions of molecular weight markers (kDa). Radiolabeling and immunoblot experiments were performed according to Alam & Hazelbauer (Alam et al., *J. Bacteriol.,* 173:5837–5842 (1991)).

FIG. 3 provides a comparison of the proteins used in the homology analyses. M1 and M2 are the site of myoglobin recognition. M2 is the site of HemAT recognition. The H-box is the primary site of microbial hemoglobin recognition.

FIG. 4 shows absorption spectra of purified HemAT-Hs, HemAT-Bs, and horseheart myoglobin (HHMb). Panel A shows oxygenated forms of purified HemAT-Hs, HemAT-Bs, and oxymyoglobin. Panel B shows deoxygenated forms of HemAT-Hs, HemAT-Bs, and myoglobin. Panel C shows CO-bound forms of HemAT-Hs, HemAT-Bs, and myoglobin. Panel D shows reoxidized forms of HemAT-Hs, HemAT-Bs. Samples concentrations are approximately 20 μM in heme. Deoxygenated samples were prepared by the addition of sodium dithionite to the deaerated protein solutions.

FIG. 5 shows aerotactic responses in *H. salinarum* and *B. subtilis*. Panel A shows *H. salinarum* strain Flx 15 (HtrVIII and HemAT-Hs present), and mutant strains ΔhemAT-Hs (HtrVIII present) and ΔhtrVIII (HemAT-Hs present). Panel B shows wild-type *B. subtilis* strain OI1085 and mutant strains OI3545 (Δten) and OI3555 (overexpression of hemAT-Bs in Δten). All cells were grown to mid-logarithmic phase. Microcapillaries (internal dimension 100×10 μm) were filled halfway with cell suspension. The capillaries were sealed at both ends and placed on a microscope stage prewarmed to 35–37° C. Time-lapse, dark-field microscopic images were recorded using video-digitized camera linked to a computer. The images shown were taken at 180 min for *H. salinarum* and at 30 min for *B. subtilis*. The meniscus at the air interface is visible to the right in each image.

Figure 6:
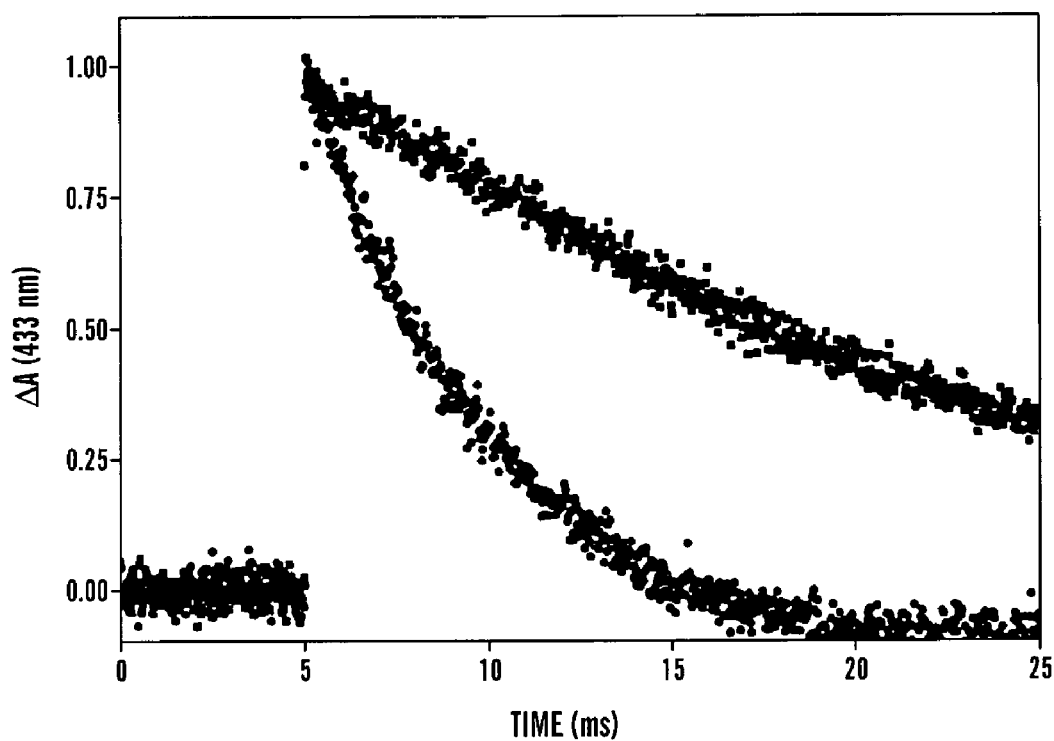

FIG. 6 provides transient absorption data subsequent to CO photolysis obtained at 430 nm at 25° C. and 1 atm CO for HemAT-Hs (solid line) and HemAT-Bs (dotted line). Samples were approximately 20 μM. The traces are the average of 50 laser pulses (532 nm exciation, 7 ns pulse width, 10 mJ/pulse).

Figure 7A:
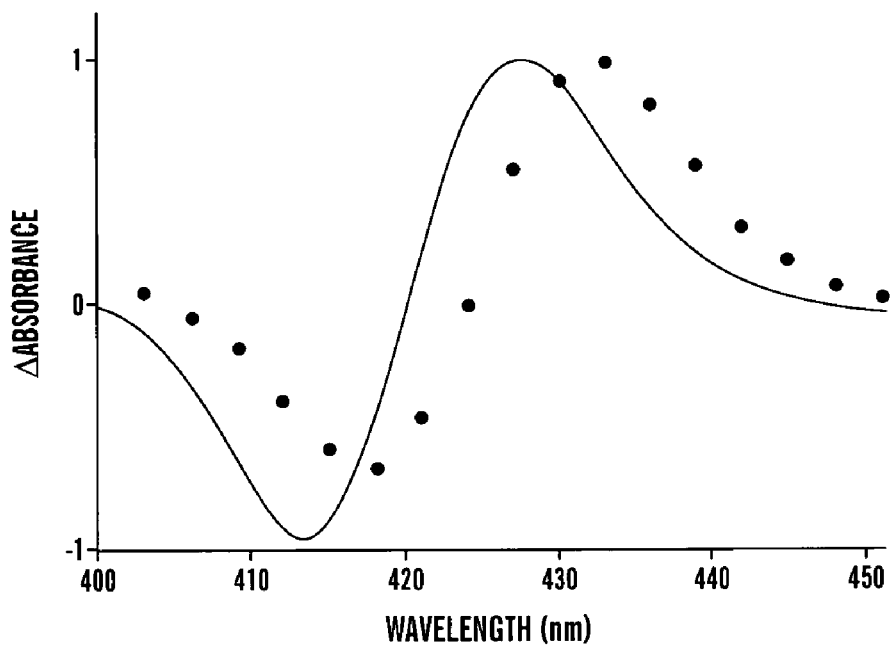
Figure 7B:
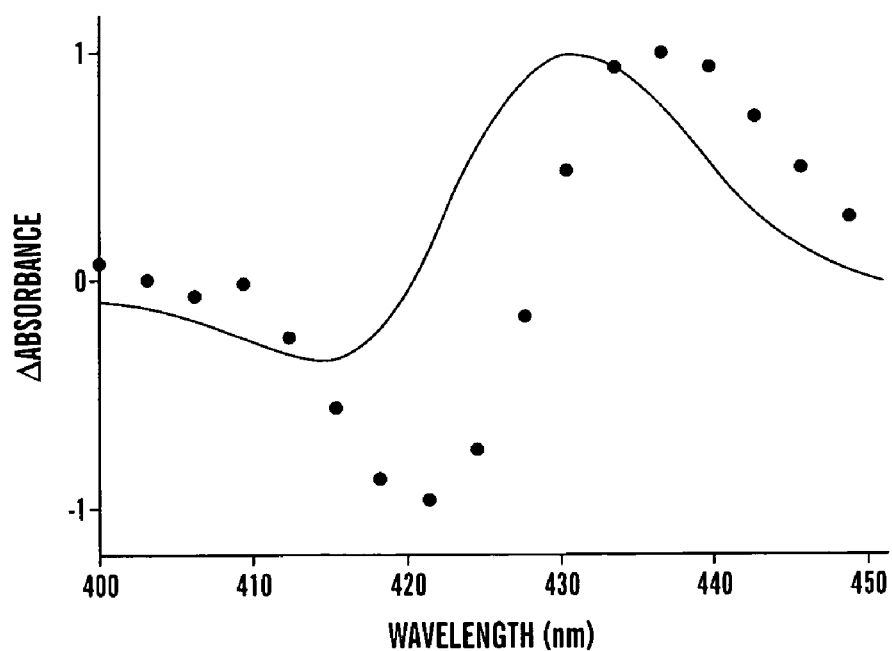

FIG. 7 shows the transient difference spectrum (25 μs subsequent to photolysis) overlaid with the equilibrium difference spectrum (deoxy minus CO-bound) for HemAT-Hs (FIG. 7A, top panel) and HemAT-Bs (FIG. 7B, bottom panel). Sample conditions are as described in FIG. 4.

DETAILED DESCRIPTION OF THE INVENTION

The present invention provides an isolated bacterial myoglobin-like heme binding protein which reversibly binds oxygen with a low affinity. These proteins are a new class of heme proteins that bind diatomic oxygen through their prosthetic group and trigger negative aerotactic responses. HemAT-Hs and HemAT-Bs are the first myoglobin-like heme proteins in the Archaea and in Bacteria, respectively. Purified HemAT-Hs and HemAT-Bs exhibit spectral properties similar to oxygen-bound myoglobin. Deoxygenation of either protein results in absorption shifts similar to those observed for deoxymyoglobin. The oxy-/deoxy spectral changes in HemAT-Hs and in HemAT-Bs are completely reversible, a characteristic feature of the heme prosthetic group in myoglobin. The C-terminus of both proteins has high homology with the signaling domain of bacterial methyl-accepting chemoreceptors and they mediate aerotaxis. By site-directed mutagenesis the fifth coordination site of the heme iron was identified in HemAT-Hs and HemAT-Bs comparable to myoglobin.

In a preferred embodiment of the invention, the isolated heme-binding protein has both a heme binding domain and a signaling domain.

Figure 1B:
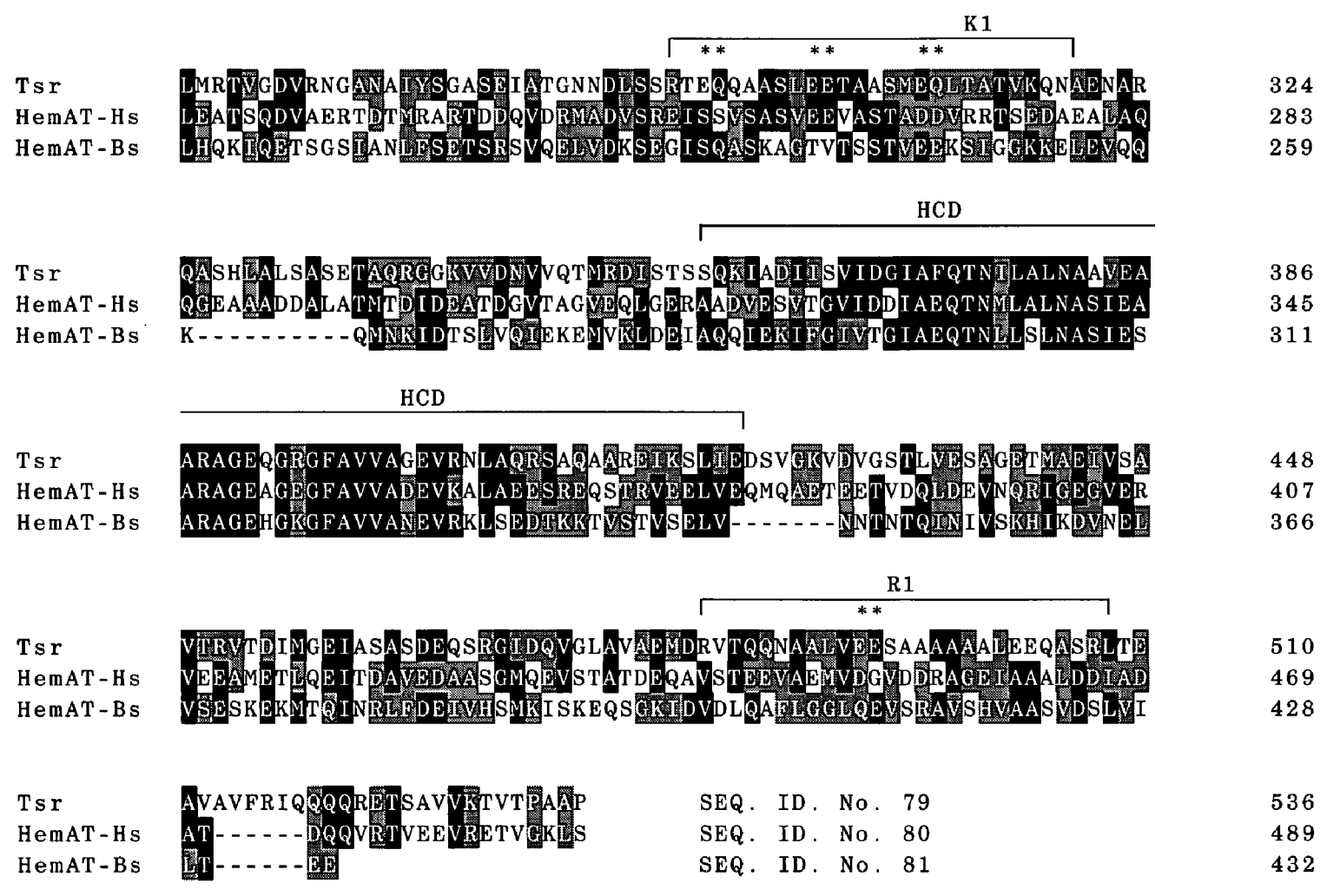

When the hemAT-Hs gene was originally cloned, its product was predicted to be a soluble signal transducer (W. Zhang et al., *Proc. Natl. Acad. Sci. U.S.A.* 93:4649 (1996), which is hereby incorporated by reference). HemAT-Bs was identified in the *B. subtilis* genome-sequencing project as the product of an open-reading frame encoding a protein with marked similarities to methyl-accepting chemotaxis proteins (MCP) (F. Kunst et al., *Nature* 390:249 (1997), which is hereby incorporated by reference). The predicted translation products of the hemAT-Hs and hemAT-Bs genes, comprising 489 and 432 residues, respectively, exhibit two striking features: a) their amino-termini (residues 1–184 in HemAT-Hs and 1–175 in HemAT-Bs) display limited homology to myoglobin (FIG. 1A); b) residues 222 to 489 of HemAT-Hs and 198 to 432 of HemAT-Bs are 30% identical to the cytoplasmic signaling domain of Tsr, an MCP from *Escherichia coli* (FIG. 1B).

The residues absolutely conserved among all globins are the proximal His in the F helix (F8) and Phe in the CD region (CD1) (B. C. Clothia, et al., *J. Mol. Biol.* 196:199 (1987); S. N. Vinogradov et al., *Comp. Biochem. Physiol.* 106B:1 (1993), which are hereby incorporated by reference). Highly conserved residues include the distal His in the E helix (E7), Phe in the CD4 region, and Pro at the beginning of the C helix (C2) (B. C. Clothia, et al., *J. Mol. Biol.,* 196:199

(1987); S. N. Vinogradov et al., *Comp. Biochem. Physiol.*, 106B:1 (1993), which are hereby incorporated by reference). Three of these residues (Pro in C2, Phe in CD1, His in F8) are conserved in both HemAT-Hs and HemAT-Bs (asterisks in FIG. 1A). These features suggested to us that HemATs may be heme-containing proteins that generate signals in response to binding of oxygen.

Both proteins, HemAT-Hs and HemAT-Bs, can be expressed in *E. coli* from recombinant vectors. PCR primers with sequences flanking the hemAT-Hs gene from *H. salinarum* strain Flx15 and encoding a NdeI or BamHI restriction site were used to amplify and clone the chromosomal gene into the pET expression vector (Novogen Inc.). The PCR product was initially ligated into the pCR$^R$-Blunt II TOPO cloning vector (Invitrogen, Inc.) and then subcloned into pET-3b after digestion of the donor and recipient plasmids with NdeI and BamHI. The resulting plasmid was introduced into the *E. coli* pLysS strain for protein expression. PCR primers with sequences flanking the hemAT-Bs gene from *B. subtilis* strain OI1085 and encoding a BamHI or PstI restriction site were used to amplify and clone the chromosomal gene into the pCR$^R$-Blunt II TOPO vector. This fragment was later subcloned into the pMALcII expression vector (New England Biolabs, Inc.), which was introduced into the *E. coli* pLysS strain for protein expression.

Recombinant HemAT-Hs is purified using anion-exchange and gel-filtration chromatography. BL21 pLysS host cells harboring plasmids carrying the hemAT-Hs or hemAT-Bs genes were grown in Luria-Bertani broth with appropriate antibiotics, and synthesis of the proteins was induced with 0.6 mM isopropyl-D-thiogalactopyranoside. After a two hour induction, the cells were harvested by low speed centrifugation (4000×g) at 4° C. for 15 min. The pellets were resuspended in buffer (50 mM NaCl, 50 mM Tris-HCl, pH 6.0) and sonicated for 4 min (12 pulses of 20 sec with 30 sec pauses). The cell lysate was centrifuged at 28,000×g for 20 min. The red supernatant became the source of proteins for purification. The HemAT-Hs supernatant was applied to an anion-exchange POROS HQ/M column equilibrated with buffer (50 mM Tris-HCl, pH 6.0). A linear gradient of NaCl (0–1500 mM) was applied, and HemAT-Hs eluted at about 400 mM. Fractions containing HemAT-Hs (monitored by the Soret band absorbance at 410 nm and SDS-PAGE) were concentrated and applied to a HiLoad Superdex 200 gel-filtration column. Fractions containing HemAT-Hs were concentrated with an Amicon 100K concentrator.

A saturated $(NH_4)_2SO_4$ solution was added to 30% saturation to the HemAT-Bs supernatant and centrifuged at 28,000×g for 20 min. The optically clear, light-red supernatant was further fractionated by adding $(NH_4)_2SO_4$ to 36% saturation, and the precipitate was pelleted by centrifugation. The pellet was resuspended in buffer (200 mM NaCl, 50 mM Tris-HCl, pH 8.0) and applied to a HiLoad Superdex 75 column. Fractions containing HemAT-Bs were concentrated with an Amicon 50K concentrator.

During SDS-polyacrylamide gel electrophoresis (SDS-PAGE), purified HemAT-Hs migrates slower than expected from its calculated molecular mass of 52.8 kDa (FIG. 2A, lane 1). This behavior is consistent with the highly acidic nature of many halophilic proteins (K. Ihara et al., *Arch. Biochem. Biophys.*, 286:111 (1991), which is hereby incorporated by reference). HemAT-Hs is purified from *H. salinarum* by metal-affinity and gel-filtration chromatography as a recombinant protein (HemAT$_{6xHis}$-Hs) carrying a carboxyl-terminal six-histidine tag (FIG. 2A, lane 2). A plasmid encoding carboxylterminal 6 His-tagged HemAT-Hs was constructed by two-step PCR. In the first step, 6 His codons were fused to hemAT-Hs immediately in front of the natural stop codon. In the second step, a XbaI restriction site was introduced at the 3' end of the gene. The second PCR product was subcloned into the NdeI and XbaI sites of plasmid pKJ427. This plasmid was introduced into a ΔhemAT-Hs strain (A. Brooun et al., *J. Bacteriol.*, 180:1642 (1998), which is hereby incorporated by reference). Cells grown at 39° C. to mid-logarithmic phase were harvested by centrifugation (4000×g) at 4° C. The pellet was resuspended in buffer (200 mM NaCl, 50 mM Tris-HCl, pH 8.0) and sonicated for 3 min (12 pulses of 15 sec with 20 sec pauses). The cell lysate was centrifuged (100,000×g) at 14° C. for 30 min, and the supernatant was used for purification. The POROS MC/M affinity column was washed with 1 M NaCl, 50 mM EDTA (pH 8.0), charged with 100 mM $CoCl_2$, and finally washed with 3 M NaCl. The column was equilibrated with buffer (200 mM NaCl, 50 mM Tris-HCl, pH 8.0) prior to loading the sample. HemAT$_{6xHis}$-Hs was eluted with a linear gradient of imidazole (0–250 mM). The peak fractions were collected, concentrated, and applied to a HiLoad Superdex 200 gel-filtration column. The peak fractions were concentrated with an Amicon 100K concentrator. HemAT-Bs is purified using a combination of ammonium-sulfate precipitation/fractionation and gel-filtration chromatography. As expected, purified HemAT-Bs migrates during SDS-PAGE as a 48.7 kDa protein (FIG. 2A, lane 3).

The preferred bacterial heme binding proteins are myoglobin-like proteins. In particular, the heme binding proteins show greater than 20% identity to a vertebrate myoglobin protein, such as sperm whale myoglobin. More preferred are proteins which show greater than 30% or 50% identity. The level of identity is calculated using the protein alignment program of BLAST with the default parameters.

In a preferred embodiment, the heme-binding protein is isolated from Archaea. The Archaea are a group of organisms often found in extreme environments, such as high temperatures, high salt concentrations, and acidic conditions. The conditions are often so extreme that other organisms are unable to survive in that environment. Proteins isolated from the Archaea often exhibit higher stability in the presence of high temperatures, high salt concentrations, or low pH. Generally, the proteins isolated from Archaea are preferred due to their higher stability.

In particular, the protein is isolated from *Halobacterium salinarum*. *H. salinarum* is a salt tolerant organism. Similarly, the HemAT-Hs protein is salt tolerant. The sequence of the gene encoding the HemAT-Hs protein is shown in SEQ. ID. No. 1 as follows:

```
ATGAGCAACG ATAATGACAC TCTCGTGACC GCCGACGTTC GGAACGGGAT CGACGGGCAC    60

GCACTCGCGG ACCGGATCGG CCTCGACGAG GCGGAGATCG CGTGGCGGCT GTCGTTCACC   120

GGGATCGACG ACGACACGAT GGCCGCGCTC GCCGCCGAAC AGCCGCTGTT CGAAGCCACC   180

GCGGACGCGC TGGTGACCGA CTTCTACGAC CACTTGGAGT CCTACGAGCG CACACAGGAC   240

CTCTTCGCGA ACTCCACGAA GACCGTCGAG CAACTCAAAG AGACGCAGGC CGAGTACTTG   300
```

-continued

| | | | | |
|---|---|---|---|---|
| CTGGGCCTCG | GGCGCGGCGA | GTACGACACC | GAGTACGCCG | CCCAGCGCGC CCGTATCGGG 360 |
| AAGATACACG | ACGTGCTCGG | GCTCGGACCG | GACGTCTATC | TGGGCGCGTA CACGCGATAC 420 |
| TACACGGGGC | TGTTGGACGC | GCTTGCCGAC | GACGTGGTCG | CCGACCGCGG CGAGGAGGCG 480 |
| GCCGCCGCCG | TCGACGAACT | CGTGGCCCGG | TTCCTGCCGA | TGTTGAAGCT GTTGACCTTC 540 |
| GATCAGCAGA | TCGCAATGGA | CACCTACATC | GACTCGTACG | CCCAGCGCCT CCACGACGAG 600 |
| ATCGACAGCC | GCCAGGAGTT | GGCGAACGCG | GTCGCCACGC | ACGTGGAAGC ACCGCTGTCC 660 |
| TCGCTGGAGG | CGACCTCGCA | GGACGTCGCC | GAGCGCACGG | ACACGATGCG GGCCCGCACC 720 |
| GACGACCAGG | TCGACCGCAT | GGCTGACGTC | AGCCGTGAGA | TATCCAGCGT GTCCGCGAGC 780 |
| GTCGAGGAGG | TCGCCTCGAC | GGCCGACGAC | GTCCGCCGGA | CCAGCGAGGA CGCCGAGGCG 840 |
| CTGGCCCAGC | AGGGCGAGGC | GGCCGCCGAC | GACGCGCTCG | CCACGATGAC CGACATCGAC 900 |
| GAGGCGACCG | ACGGCGTCAC | CGCGGGCGTC | GAACAGCTCG | GCGAGCGCGC CGCCGACGTC 960 |
| GAATCAGTGA | CCGGCGTGAT | CGACGACATC | GCCGAGCAGA | CGAACATGCT GGCGCTGAAC 1020 |
| GCGTCCATCG | AGGCCGCCCG | CGCCGGGGAG | GCGGGCGAGG | GGTTTGCGGT CGTCGCCGAC 1080 |
| GAGGTCAAGG | CCCTCGCCGA | GGAGTCCCGC | GAGCAGTCCA | CGCGCGTCGA GGAGCTCGTC 1140 |
| GAGCAGATGC | AGGCGGAGAC | CGAGGAGACG | GTCGACCAGT | TGGACGAGGT CAACCAGCGC 1200 |
| ATCGGCGAGG | GCGTCGAGCG | CGTCGAGGAG | GCGATGGAGA | CCCTCCAGGA GATCACCGAC 1260 |
| GCCGTCGAGG | ACGCCGCAAG | CGGGATGCAG | GAGGTGTCGA | CGGCGACCGA CGAACAGGCG 1320 |
| GTGAGCACCG | AGGAGGTCGC | CGAGATGGTC | GACGGTGTCG | ACGACCGCGC GGGCGAGATC 1380 |
| GCGGCCGCCC | TCGATGACAT | CGCCGACGCG | ACCGATCAGC | AGGTCCGGAC CGTCGAGGAG 1440 |
| GTCCGCGAGA | CGGTCGGCAA | GCTCAGCTAG | | 1470 |

The hemAT-Hs gene encodes a protein which has an amino acid sequence as shown in SEQ. ID. No. 2 as follows:

| | |
|---|---|
| MSNDNDTLVTADVRNGIDGHALAD-<br>RIGLDEAEIAWRLSFTGIDDDTMAALAAEQPLFEAT | 60 |
| ADALVTDFYDHLESYERTQDLFANSTK-<br>TVEQLKETQAEYLLGLGRGEYDTEYAAQRARIG | 120 |
| KIHDVLGLGPDVYLGAYTRYYTGLLDAL-<br>ADDVVADRGEEAAAAVDELVARFLPMLKLLTF | 180 |
| DQQIAMDTYIDSYAQRLH-<br>DEIDSRQELANAVATHVEAPLSSLEATSQDVAERTDTMRART | 240 |
| DDQVDRMADVSREISSVSASVEEVAS-<br>TADDVRRTSEDAEALAQQGEAAADDALATMTDID | 300 |
| EATDGVTAGVEQLGERAADVESVTGVID-<br>DIAEQTNMLALNASIEAARAGEAGEGFAVVAD | 360 |
| EVKALAEESREQSTRVEELVEQMQA-<br>ETEETVDQLDEVNQRIGEGVERVEEAMETLQEITD | 420 |
| AVEDAASGMQEVSTATDEQAVSTE-<br>EVAEMVDGVDDRAGEIAAALDDIADATDQQVRTVEE | 480 |
| VRETVGKLS | 489 |

In another embodiment of the invention, the heme-binding protein is isolated from *Bacillus subtilis*. Preferably, the *Bacillus subtilis* gene is hemAT-Bs, which has a nucleic acid sequence according to SEQ. ID. No. 3, as follows:

```
ATGTTATTTA AAAAAGACAG AAAACAAGAA ACAGCTTACT TTTCAGATTC AAACGGACAA      60
CAAAAAAACC GCATTCAGCT CACAAACAAA CATGCAGATG TCAAAAAACA GCTCAAAATG     120
GTCAGGTTGG GAGATGCTGA GCTTTATGTG TTAGAGCAGC TTCAGCCACT CATTCAAGAA     180
AATATCGTAA ATATCGTCGA TGCGTTTTAT AAAAACCTTG ACCATGAAAG CTCATTGATG     240
GATATCATTA ATGATCACAG CTCAGTTGAC CGCTTAAAAC AAACGTTAAA ACGGCATATT     300
CAGGAAATGT TTGCAGGCGT TATCGATGAT GAATTTATTG AAAAGCGTAA CCGAATCGCC     360
TCCATCCATT TAAGAATCGG CCTTTTGCCA AAATGGTATA TGGGTGCGTT TCAAGAGCTC     420
CTTTTGTCAA TGATTGACAT TTATGAAGCG TCCATTACAA ATCAGCAAGA ACTGCTAAAA     480
GCCATTAAAG CAACAACAAA AATCTTGAAC TTAGAACAGC AGCTTGTCCT TGAAGCGTTT     540
CAAAGCGAGT ACAACCAGAC CCGTGATGAA CAAGAAGAAA AGAAAAACCT TCTTCATCAG     600
AAAATTCAAG AAACCTCTGG ATCGATTGCC ATTCTGTTTT CAGAAACAAG CAGATCAGTT     660
CAAGAGCTTG TGGACAAATC TGAAGGCATT TCTCAAGCAT CCAAAGCCGG CACTGTAACA     720
TCCAGCACTG TTGAAGAAAA GTCGATCGGC GGAAAAAAAG AGCTAGAAGT CCAGCAAAAA     780
CAGATGAACA AAATTGACAC AAGCCTTGTC CAAATCGAAA AGAAATGGT CAAGCTGGAT      840
GAAATCGCGC AGCAAATTGA AAAAATCTTC GGCATCGTCA CAGGCATAGC TGAACAAACA     900
AACCTTCTCT CGCTCAATGC ATCTATTGAA TCCGCCCGCG CCGGAGAACA CGGCAAAGGC     960
TTTGCTGTCG TGGCAAATGA AGTGCGGAAG CTTTCTGAGG ATACGAAAAA AACCGTCTCT    1020
ACTGTTTCTG AGCTTGTGAA CAATACGAAT ACACAAATCA ACATTGTATC CAAGCATATC    1080
AAAGACGTGA ATGAGCTAGT CAGCGAAAGT AAAGAAAAAA TGACGCAAAT TAACCGCTTA    1140
TTCGATGAAA TCGTCCACAG CATGAAAATC AGCAAAGAGC AATCAGGCAA AATCGACGTC    1200
GATCTGCAAG CCTTTCTTGG AGGGCTTCAG GAAGTCAGCC GCGCCGTTTC CCATGTGGCC    1260
GCTTCCGTTG ATTCGCTTGT CATCCTGACA GAAGAATAAC CATCAAAAAC CGGTCTGCCA    1320
TACGGCCGGT TTTTTTGCGT TCATTATGTA AACTTAAATT AAAAATCAGT TGACATAATA    1380
ATTACCTGCA                                                           1390
```

In a preferred embodiment, the protein has an amino acid sequence of SEQ. ID. No. 4, as follows:

```
MLFKKDRKQETAYFSDSNGQQKNRIQLTNKHADVKKQLKMVRLGDAELYVLEQLQPLIQE      60
NIVNIVDAFYKNLDHESSLMDIINDHSSVDRLKQTLKRHIQEMFAGVIDDEFIEKRNRIA     120
SIHLRIGLLPKWYMGAFQELLLSMIDIYEASITNQQELLKAIKATTKILNLEQQLVLEAF     180
QSEYNQTRDEQEEKKNLLHQKIQETSGSIANLFSETSRSVQELVDKSEGISQASKAGTVT     240
SSTVEEKSIGGKKELEVQQKQMNKIDTSLVQIEKEMVKLDEIAQQIEKIFGIVTGIAEQT     300
NLLSLNASIESARAGEHGKGFAVVANEVRKLSEDTKKTVSTVSELVNNTNTQINIVSKHI     360
KDVNELVSESKEKMTQINRLFDEIVHSMKISKEQSGKIDVDLQAFLGGLQEVSRAVSHVA     420
ASVDSLVILTEE                                                     432
```

The invention also provides fragments of the isolated heme-binding protein which contain a functional heme-binding domain. The fragment containing the functional heme-binding domain may be coupled to a heterologous signal transduction domain. As described in the examples, a minimum heme binding domain has been determined for HemAT-Hs and partially determined for HemAT-Bs. Furthermore, comparisons beteween various globin proteins has allowed for the identification of conserved regions of the proteins.

HemAT-Hs in *Halobacterium salinarum* and HemAT-Bs in *Bacillus subtilis*, the first aerotactic transducers discovered that directly bind oxygen, are heme-based, and are homologous to native sperm whale myoglobin (SWMb), albeit more structural than sequential. These proteins belong to the globin family. Globins bind, transport, and store oxygen, and are known to exhibit a distinctive fold of seven α-helices that encompass a heme prosthetic group. The seven helices are labeled A, B, C, E, F, G, and H. Sometimes, an additional short helix (helix D) is found between helices C and E, as in the case of SWMb, to make a total of eight. In a 1987 publication, Bashford et al., "Determinants of a Protein Fold: Unique Features of the Globin Amino Acid Sequences," *J. Mol. Biol.*, 196:199–216 (1997), which is hereby incorporated by reference, reported that the sequence homology of all the 226 globin sequences known at that time were "as high as 80% or more for closely related species, or as low as 16% for more distant ones." Of all these proteins, only two residues were absolutely conserved throughout. These two residues were the phenylalanine at the end of the C helix (CD 1) and the proximal histidine (F8). HemAT-Hs and HemAT-Bs both contain these two key residues and are 23% and 11% homologous to SWMb, respectively, and share 20% sequence similarity between themselves.

The report of myoglobin-type aerotaxis proteins in microorganisms, and the recent discovery of HemAT-Hs and HemAT-Bs has prompted an effort to find one or more signature motifs in these possible microbial globins. These would identify conserved regions the proteins. In addition, with these motifs in hand, contemporary computer algorithms like those contained in the BLAST programs could permit convenient and rapid searches for other possible globins using this signature motif. These motifs could be used for classifying these newly discovered microbial globins together and eventually with the whole globin family.

Vianogradov et al., "Adventitious Variability? The Amino Acid Sequences of Nonvertebrate Globins," *Comp. Biochem. Physiol.*, 106B:1–26 (1993), which is hereby incorporated by reference, have noted the extensive variation of invertebrate globins over the vertebrates and Bashford et al., "Determinants of a Protein Fold: Unique Features of the Globin Amino Acid Sequences," *J. Mol. Biol.*, 196:199–216 (1987), which is hereby incorporated by reference, have recognized that alignments of invertebrate globins with vertebrate globins based strictly on sequence similarity and vertebrate data sets are questionable. Invertebrate myoglobins were therefore not included in the preliminary data and the search for a globin motif was limited to vertebrates. Microbial globins, however, were later included and incorporated into the alignment by conserving secondary structure and avoiding gaps as in the work of Kapp et al., "Alignment of 700 Globin Sequences: Extent of Amino Acid Substitution and Its Correlation With Variation in Volume," *Pro. Sci.*, 4:2179–2190 (1995), which is hereby incorporated by reference.

An 80-aa consensus peptide sequence was constructed using the manual alignment of sperm whale myoglobin (SWMb), the oxygen sensor in *Bacillus subtilis*, HemAT-Bs, and the oxygen sensor in *Halobacterium salinarum*, HemAT-Hs. The intent was to find a minimal length of protein containing the myoglobin signature motif and see how many myoglobin proteins this sequence would recognize on the non-redundant (nr) database at NIH using the BLAST server. An X was issued to residues of high variability (Bashford et al., "Determinants of a Protein Fold: —Unique Features of the Globin Amino Acid Sequences," *J. Mol. Biol.*, 196:199–216 (1987), which is hereby incorporated by reference) while conserved residues retained their specific amino acid designation. Critical to the alignment was the positioning of the two residues known to be absolutely conserved in all known globins: Phe at the CD1 position and the proximal His at the F8 position (Bashford et al., "Determinants of a Protein Fold: Unique Features of the Globin Amino Acid Sequences," *J. Mol. Biol.*, 196:199–216 (1987), which is hereby incorporated by reference). Using these residues as markers, the myoglobin-like protein (MbLP) sequence was generated and consisted of two domains separated by 32 variable amino acids. The first myoglobin-type domain (M1-box) contained the absolutely conserved phenylalanine residue; the second (M2-box) contained the absolutely conserved proximal histidine. A BLAST search was then performed, comparing the sequences of MbLP and SWMb with those of all other proteins in the non-redundant database. Search parameters were default except for the EXPECT parameter, which was increased to 1000 to allow for matches of lesser sequence homology. This comparison between the number and type of SWMb hits and MbLP hits was used to assess the quality of the MbLP sequence in extracting myoglobin proteins.

A microbial globin-type sequence was generated from the results of a previous BLAST search on microbial globins and included *Vitreoscilla* hemoglobin for structural markers. This sequence was used to extract 9 bacterial and 8 eukaryotic hemoglobins and flavohemoproteins. This sequence was generated to incorporate microbial globins into the search of a combined globin motif. Manipulation and alignment of the microbial globin-type peptide with MbLP and incorporating the same marker residues produced a second consensus sequence 96-amino acids in length called the triplet globin motif (TGM) because it consisted of three domains: two myoglobin-type domains (M1-box, M2-box) and one hemoglobin-type domain (H-box). TGM was the final sequence used for further analysis and BLASTP searches with the TGM sequence were performed at a lower EXPECT parameter of 600 to reduce the amount of false-positives.

The ability of the myoglobin motif to recognize myoglobins was tested using SWMb as a reference. A BLASTP search of the non-redundant protein database was performed using the 153-aa native sperm whale myoglobin (SWMb) as the query sequence. This sequence recognized 83 unique myoglobins and a wealth of hemoglobins. With some manipulation of the search conditions, however, SWMb was able to extract HemAT-Hs as well.

A first attempt at a globin-type motif produced the 80-aa myoglobin-like protein (MbLP) sequence consisting of two domains, the M1-box and M2-box, as found in FIG. 3. These two domains recognized 73 myoglobins, or 88% of those found by SWMb, along with HemAT-Hs, HemAT-Bs, and a few non-globins. In contrast, however, MbLP didn't recognize any hemoglobins.

An effort was made to enhance the globin-type motif of MbLP by building upon itself. This effort resulted in the 96-aa triplet globin motif (TGM) protein sequence and consisted of three domains: the M1-, M2-box, and a new H-box situated in front of the two. The TGM sequence was compared to the MbLP and SWMb by subjecting it to the same BLASTP search analysis. TGM recognized 75 myoglobins (90% of SWMb hits), 17 hemoglobin and hemoglobin-like proteins, and the two HemATs. The 17 hemoglobin and hemoglobin-like proteins consisted of 5 non-microbial eukaryotic hemoglobins from three different organisms and 12 microbial hemoglobins, three eukaryotic and nine bacterial. It is evident that the TGM sequence is more general than MbLP in recognizing globin motifs.

TABLE 1

Alignment and classification of some of the resultant proteins in the H-box and M1-box region using TGM as the template. Shaded residues are conserved in their respective box (H-, M1-, M2-box). Bold residues are highly conserved in their box.

```
Kingdom Globin   Secondary (SWMb ->)           HHHHHHHHHHHhHHHHHHHHHHHHHHHHHHHHHHHhhhhhhhhhhhllllllllHHHHHHHHHhhhhhh
                                               |<    A    >|<    B    >|<  C  >|    . M1 Box       >|<  D  >|<       E
                                                   H Box                                             M1 Box
         Template    tmpseq_1    1              IIKXTVPVLKEHGXXIGQDVLVVLIIKKNPEIQ-EKX--FFXKHXXXXXXXXXXXXXXXX  57   SEQ. ID. No.  5
B   H    HMPA_ERWCH  Q47266     10              IKSTIPLLAETGPALTAHFYQRMFTHHNPELK-DIX--NMSNQRNGDQREALFNAICAY  64   SEQ. ID. No.  6
B   H    BAHG_VITST  P04252      9              IIKATVPVLKEHGVTITTTFYKNLFAKHPEVR-PLX--DMGRQESLEQPKALAMTVLAA  64   SEQ. ID. No.  7
B   H    HMPA_ECOLI  P24232     10              VKATIPLLVETGPKLTAHFYDRMFTHNPELK-EIX--NMSNQRNGDQREALFNAIAAY  64   SEQ. ID. No.  8
B   H    FHG_SMNLA   2738912    10              VKATIPLLVETGPKLTAHFYDRMFTHNPELK-EIX--NMSNQRNGDQREALFNAIAAY  64   SEQ. ID. No.  9
B   H    HMPA_ALCEU  P39662      9              IVKATAPVLAEHGYDIIKCFYQRMFEAHPELK-NVX--NMAHQEQGQQQALARAVAY   64   SEQ. ID. No. 10
B   H    HMPA_VIBPA  P40609      9              IVKATAPLIAETGPKLTAHFYDRMFTHNPELK-DIX--NMSNQRNGDQREALFNAICAY 64   SEQ. ID. No. 11
B   H    BAHG_CLOS   BAA81644    9              IIKSTVPVLKSNGLEITKTFYKNMFEQNPEVK-PLX--NMNKQESEEQPKALAMAILAV 64   SEQ. ID. No. 12
B   H    FHG_FUOXY   BAA33011   10              IVKSTAPILKEHGKTITTTFYRNMLGAHPELK-NYX--SLRNQQTGAQQAALANSVLAY 65   SEQ. ID. No. 13
B   H    FHP_AQUAE   2982927     9              VIKSTVPLLKEHGTEITTARMYELLFSKYPKTK-ELX--AGA---SEEQPKKLANAIIAY 61   SEQ. ID. No. 14
B   H    HMPA_BACSU  P49852      9              IIKSTVPVLQQHGETITGRFYDRMFQDHPELL-NIX--NQTNQKKKTQRTALANAVIAA 64   SEQ. ID. No. 15
B   H    HGA1_XENO   CAA32474   11              IKAIMPSIAAHGDTFGEALYRMFLVNPKTK-TYXPSFDFHHNSK-QITSHGKKVVDA   66   SEQ. ID. No. 16
B   E    GLB8_CHITH  P02227      8              DQLALFKSSWNTVKHNEVDILYAVFKANPDIQ-ARXQFAGKDLDSIKDSADF-AVHSG  64   SEQ. ID. No. 17
B   E    HBA1_XENBO  P07430     11              IKAIMPSIAAHGDKFGEALYRMFLVNPKTK-TYXPTFDFHHNSK-QISAHGKKVVDA   66   SEQ. ID. No. 18
B   E    HBA2_XENBO  P07431     11              IKAILPSIAAHGDKFGEALYRMFLINPKTK-TYXPNFDFHHNSK-QISAHGKKVVDA   66   SEQ. ID. No. 19
B   E    GLB11_CHIT  2155298    24              QAILIRSSWEDEVKHNEVDILYAIFKANPDIQ-ARXQFAGKDLDSIKTTGQF-AVHAG  79   SEQ. ID. No. 20
B   H    FHP_CANNO   Q03331     21              LQSLAPVVKEHGVTVTSTMYKYMFQTYPEVR-SYX--NMTNQKTGRQPKVLAFSLYQY  75   SEQ. ID. No. 21
B   H    FHG_YEAST   S57699      9              IIKATVPVLEQQGTVITRTFYKNMLTEHTELI-NIX--NRTNQKVGAQPNALATTVLAA 64   SEQ. ID. No. 22
E   M    MYG_PHYCA   P02185     25              XQDILIRLFKSHPETL-EKX--DRXKHLKTEAEMKASEDLKKHG                65   SEQ. ID. No. 23
E   M    MYG_KOGSI   P02184     25              XQDILIRLFKHHPETL-EKX--DRXKHLKTEAEMKASEDLKKHG                65   SEQ. ID. No. 24
E   M    MYG_ROUAE   P02163     25              XQEVLIRLFKGHPETL-EKX--DKXKHLKTEAEMKASEDLKKHG                65   SEQ. ID. No. 25
E   M    MYG_TURTR   P02172     25              XQDVLIRLFKGHPETL-EKX--DKXKHLKTEAEMKASEDLKKHG                65   SEQ. ID. No. 26
E   M    MYG_GLOME   P02174     25              XQDILIRLFKGHPETL-EKX--DKXKHLKTEAEMKASEDLKKHG                65   SEQ. ID. No. 27
E   M    MYG_WHAUK   JT0636     25              XHQVLMRLFQDHPETL-DRX--DKXKGLKTPDQMKGSEDLKKHG                65   SEQ. ID. No. 28
E   M    MYG_MUSAN   P14399     21              QNILLLRLFEQYPESQ-NHX--PKXKN--KSLGELKDTADIKAQ                59   SEQ. ID. No. 29
```

TABLE 2

Alignment and classification of some of the resultant proteins
in the M2-box region using TEMPLATE as the template.
Shaded residues are conserved in their respective boxes (H-, M1-, M2-box).

```
Kingdom Globin Secondary              hhhhhhhhhhhhl11111111HHHHHHHHHHH1111hhhhh
                                       E        >|            |<   F     >|    |< G
                                                               |<     M2 Box        >|
              TEMPLATE    tmpseq_1  58 XXXXXXXXXXXXXXXXXXXAQRXR-LAQIHAXKGKIPDWYL  96  SEQ. ID. No. 30
        E  M  MYG_PHYCA   P02185    66 VTVLTALGAILKKKGHHEAELKP-LAQSHATKHKIPIKYL  104  SEQ. ID. No. 31
        E  M  MYG_KOGSI   P02184    66 VTVLTALGAILKKKGHHEAELKP-LAQSHATKHKIPIKYL  104  SEQ. ID. No. 32
        E  M  MYG_ROUAE   P02163    66 ATVLTALGGILKKKGQHEAQLKP-LAQSHATKHKIPIKYL  104  SEQ. ID. No. 33
        E  M  MYG_TURTR   P02172    66 NTVLTALGAILKKKGHHDAELKP-LAQSHATKHKIPIKYL  104  SEQ. ID. No. 34
        E  M  MYG_GLOME   P02174    66 NTVLTALGAILKKKGHHEAELKP-LAQSHATKHKIPIKYL  104  SEQ. ID. No. 35
        E  M  MYG_WHAUK   JT0636    66 VTVLTQLGKILKQKGNHESELKP-LAQSHATKHKIPIKYL  104  SEQ. ID. No. 36
        E  M? HemAT-Bs    CAA745545  96 LKRHIQEMFAGVIDDEFIEKRNR-IASIHLRIGLLPKWYM  134  SEQ. ID. No. 37
        E  M  MYG_MUSAN   P14399    60 ADTVLSALGNIVKKKGSHSQPVKALAATHITTHKIPPHYF  99   SEQ. ID. No. 38
        A  M? HemAT-Hs    1654421    96 QAEYLLGLGRGEYDTEYAAQRAR-IGKIHDVLGLGPDVYL  134  SEQ. ID. No. 39
```

The secondary structure reported in FIG. 3 is that of SWMb and is considered typical of the globins. It was interesting to note that the domain responsible for HemAT recognition, the M2-box, lies in the region between the F and G helix, which contains the proximal histidine. Alignments indicate that two loop regions of the HemATs (CD and EF loops) are much more extensive than in SWMb. The M2-box does not include the HemATs' distinctive EF loop, thereby allowing recognition of both of the transducers. The M1-box not only includes the B and C helix, but also specifies the entire CD loop region, which, inadvertently, ends up excluding the HemATs.

The H-box recognizes primarily microbial hemo-globins/proteins, which is equivalent in position to the last two-thirds of helix A and the first third of helix B of SWMb. This region is highly significant, as it is could help place a sequence like TEMPLATE man phylogenetic tree, thereby connecting the eukaryotic and eubacterial hemoglobins with the myoglobins and myoglobin-like proteins. The M1-box, containing what would be helices B and C from SWMb, incorporates one of the absolutely conserved residues, Phe, from the CD region and only pulls out myoglobins from higher species. Though the match scores are much lower, the M2-box pulls out almost the same myoglobins as the M1-box, however, recognition of HemAT-Hs and HemAT-Bs occurs only in the M2-box.

Based upon the extensive information available regarding conserved structures in the proteins, as well as the minimal functional regions, one can predict modifications to the proteins which will not alter the function of the protein.

The present invention also provides a blood substitute. An urgent need exists among the medical community for an alternative to whole blood or red blood cells for use in transfusion. However, the possibility of transmitting viral infections is ever present in derivatives of human blood. The rapid spread of the AIDS virus as well as the discovery of multiple forms of the virus amplifies this concern. Both HemAT-Hs and/or HemAT-Bs may present an alternative to whole blood in transfusion situations. HemAT-Hs and HemAT-Bs are particularly attractive in this regard, since they appear to have low oxygen affinity, a property required for artificial oxygen carriers. Expressed in microorganisms, these oxygen carriers will be free of infectious agents. In addition, the ability of HemAT-Hs and HemAT-Bs to bind oxygen reversibly and to regulate this binding through the signal transduction domain may lead to new blood substitute products. Currently crosslinked hemoglobins are being developed as blood substitutes but these proteins suffer from poor regulation of oxygen binding. It is possible to develop HemAT-Hs and HemAT-Bs as a "blood-substitute" due to their size (~50 kDa, similar to hemoglobin) which prevents filtering by the kidney's, its ability to reversibly bind oxygen, and its ability to regulate this binding. Genetically engineered fragments of the hemAT-Hs and hemAT-Bs genes that encode of the transduction domain provides a wealth of opportunities to regulate oxygen binding.

In a preferred embodiment, the blood substitute has a heme binding domain of the isolated heme-binding protein. The blood substitute may also have a heterologous signal transduction domain, to alter the affinity for oxygen or other gases.

The blood substitute may be administered to a patient suffering from low blood levels. Such a blood substitute has numerous advantages because it could be used as a substitute when whole blood is not available. Furthermore, the blood substitute can be produced so that it is free of infectious substances, such as viruses and bacteria.

In addition to using heterologous signaling domains, the oxygen binding of the heme-binding protein may be altered by modifying the signaling domain.

The invention also provides a method for controlled storage of oxygen. The bacterial heme binding protein can be contacted with oxygen allowing the protein to bind and store oxygen. The protein may also be covalently attached to a solid substrate via the transduction domain. Subsequent triggering of the transduction domain can result in oxygen release.

The present invention may also be used to sense gaseous ligands by exposing the bacterial heme binding protein to a sample to be tested and measuring a change in the conformation of the protein. Enzyme sensors are well known as biological sensors. They are utilized mainly for clinical chemical analysis, including use for glucose in blood, urea and neutral and phospholipids. The ability of HemAT-Hs and HemAT-Bs to sense oxygen as well as other small gaseous ligands provides opportunities to develop novel biosensors for $O_2$, NO, CO, and even $CN^-$.

The changes in the conformation of the protein may be monitored in various ways including monitoring the protein optically or electronically.

The preferred gaseous ligands to monitor with the heme binding bacterial protein are $O_2$, NO, CO, and $CN^-$. The preferred gaseous ligand is $O_2$.

As discussed above fragments of the bacterial heme binding protein may also be used as long as they contain a functional heme binding domain.

The present invention also provides a chimeric protein having a heme-binding domain of an isolated heme binding bacterial protein and a heterologous signaling domain. Varying the signaling domain can alter the oxygen or ligand binding characteristics of the protein. The signaling domain may also be altered to make the protein responsive to other signals.

In another embodiment, the invention provides an isolated nucleic acid molecule which encodes a bacterial heme binding protein with a heterologous or mutated signaling domain.

The bacterial heme-binding proteins may also be used for heme-based catalysis. It is well known that Fe(III)porphyrins can catalyze a wide variety of chemical reactions including hydrogen peroxide degradation, mono oxygenation, and lignin degradation. HemAT-Hs can also be prepared in the Fe(III) form providing an opportunity to utilize this protein as a novel heme-based catalyst. In addition, the ability to regulate the heme domain by the transduction domain may allow for catalytic specificity to be achieved via genetic manipulation of this domain.

The proteins of the present invention may also be used for artificial photosynthesis. HemAT-Hs can be reconstituted with different porphyrins including photoactive Zn and Sn derivatives. These derivatives may posses the ability to absorb light energy and transmit information concerning the excited state of the photoactive poprhyrin to the sensing domain providing-the equivalent to photosynthesis, i.e., conversion of light energy to chemical potential energy.

The bacterial heme binding proteins may also be used in in vivo and in vitro testing system for identifying potential signaling functions of mutated a-hemoglobin and myoglobin causing several diseases. Mutated human α-hemoglobin and myoglobin genes can be fused with fragment of hemAT-Hs or hemAT-Bs genes that encodes signaling domain via linker region. The physiological function of the expressed chimeric protein of human α-hemoglobin (or myoglobin) and HemAT-Hs or HemAT-Bs can be tested by capillary aerotaxis assay. As transducer proteins HemAT-Hs and HemAT-Bs may cause phosphorylation of CheA. Once this feature of HemAT-Hs and HemAT-Bs are tested and optimized, similar in vivo strategy of chimeric protein construction can be tested for in vitro phosphorylation assay.

EXAMPLES

Example 1

Mutagenesis of HemAT-Hs and HemAT-Bs

The HtrVIII is a positive aerotaxis transducer in *H. salinarum* (Broown et al., *J. Bacteriol.*, 180:1642–1646 (1998), which is hereby incorporated by reference). A strain deleted for the htrVIII gene lacks positive aerotaxis while a strain overproducing the protein shows an enhanced aerotactic response. To investigate the possible role of HemAT-Hs and HemAT-Bs in aerotaxis, deletion mutants of these genes were constructed (Broown, Ph.D thesis. University of Hawaii, Hawaii (1997), which is hereby incorporated by reference) for the construction of hemAT-Hs deletion strains. Construction of overexpression of hemAT-Hs in *H. salinarum*: NdeI and XbaI restriction sites were used to clone the hemAT-Hs gene into the *E. coli-H. salinarum* shuttle vector pKJ427. Top primer with NdeI cutting site (5'CCGAATTCCATATGAGCAACGAT AATGAC 3' (SEQ. ID. No. 40)) and bottom primer with XbaI cutting site (5'CCTCTA GAGGATNNCTAGCTGAGCTTGCCGACC 3' (SEQ. ID. No. 41)) were synthesized and used for PCR amplification of hemAT-Hs gene. The PCR amplicon was cloned into TOPO cloning vector (Invitrogen) and transformed into *E. coli* competent cells. The plasmid containing hemAT-Hs gene in TOPO vector was subcloned into pKJ427 vector by NdeI/XbaI double digestion. The hemAT-Hs/pKJ427 construction was confirmed by PCR as well as NdeI/XbaI double digestion and transformed into ΔhtrVIII strain using standard halobacteria transformation protocol. Individual colonies were checked by PCR and immunoblot to confirm the expression level of HemAT-Hs; Construction of OI3428: A 322 bp fragment interior to HemAT-Bs was amplified from the *B. subtilis* wild type strain OI1085 chromosome using primers with overhanging HindIII and BamHI sites (reverse primer: 5' TATGGGATCCCTTGT-TCATCACGGGTCTNTTGG 3' (SEQ. ID. No. 42), forward primer: 5' GATAAAGCTTGATCATAGCTCAGTTGACCG 3' (SEQ. ID. No. 43)). This PCR fragment was digested with HindIII and BamHI and cloned in the integration vector pHV501 (Vagner et al., *Microbiology*, 144(Pt 11):3097–3104 (1998)) to create pMK1. The resultant plasmid pMK1 was transformed into OI1085 and HemAT-Bs mutants were selected by erythromycin resistance. Integration of the pMKI into the correct locus was checked by linkage analysis. The hemAT-Bs locus is 30% linked to the glyk locus as determined from the *B. subtilis* chromosomal map. GLY+transductants were selected and scored for erythromycin resistance. Construction of OI3498: The entire HemAT-Bs gene including the native promoter and the ribosome binding site was amplified from the *B. subtilis* wild type strain OI1085 chromosome using primers with overhanging EcoRI and BamHI sites (HemAT-Bs amyup: 5' TGCTGAATTCGCAGCTTTCATTCATGTTTCCC 3' (SEQ. ID. No.44), HemAT-Bs amydown: 5' TTAGGGATC-CGTCAACTGATTTTTAA TTTAAGTTAC 3') (SEQ. ID. No. 45)). The PCR amplicon was digested with EcoRI/BamHI and cloned into the amyE integration vector pDG1730 (Guerout-Fleury et al., *Gene*, 180(1–2):57–61 (1996), which is hereby incorporated by reference) to produce pKZ2. The resultant plasmid pKZ2 was digested with BglI/XbaI to ensure a double crossover event into the amyE locus and then transformed into OI3428 to select for Spec-R. HemAT-Bs overexpression R4: Overexpression construction in *E. coli*: The HemAT-Bs overexpression construction was performed as follows: *B. subtilis* OI1085 genomic DNA was used for the PCR amplification of HemAT-Bs gene by Pfu DNA polymerase using two primers (Top primer with BamHI restriction site: 5'ATATGGATCCAAGGGGGAT-CATTGTAATGTTA TTTAAAAAAG 3' (SEQ. ID. No. 46), Bottom primer with PstI site: 5' ATTACTGCAGCA ACT-GATTTTTAATTTAAGTTTACATAATGAACGC 3' (SEQ. ID. No. 47)). The PCR amplicon was cloned into TOPO cloning vector (Invitrogen) and transformed into TOP 10 *E. coli* competent cells. Colonies were tested for the presence of plasmids containing the correct insert. The recombinant plasmid was digested with BamHI and PstI and the insert with HemAT-Bs open reading frame was cloned into the pMALcII expression vector (New England Biolabs, Inc).

Example 2

Aerophilic and Aerophobic Responses

Figure 5A:
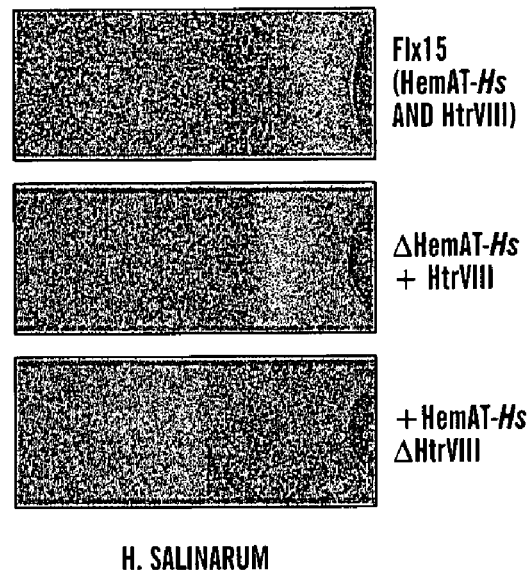
Figure 5B:
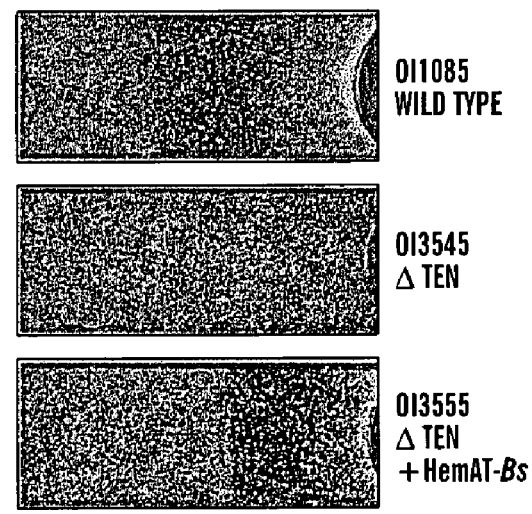

The resultant construct was transformed to *E. coli* pLysS cells for the expression and analyzed their behavior in a flat microcapillary using dark-field microscope coupled with time-lapse digital video system. Motile wild-type halobacterial cells form two clear congregated aerotactic bands, a positive one close to the interface between air and cell suspensions and a negative one away from the interface (FIG. 5A, wild type). The positive aerotactic band is mediated by HtrVIII (Brooun et al., *J. Bacteriol.*, 180:1642–1646 (1998), which is hereby incorporated by reference). As expected, this phenomenon is absent in the htrVIII deletion strain (FIG. 5A, HemAT-Hs+ΔHtrVIII). However, like the wild type strain, the ΔHtrVIII strain also demonstrates the negative aerotactic band. If negative aerotaxis behavior is related to HemAT-Hs, one would postulate that in the hemAT-Hs deletion strain, the negative aerotactic band would not form. Indeed, in the ΔhemAT-Hs strain, in which the positive aerotactic band is present due to the receptor HtrVIII, the sharp boundary of the negative aerotactic band is absent (FIG. 5A, ΔhemAT-Hs) Furthermore, when HemAT-Hs is overexpressed (using a multicopy plasmid) in a ΔhtrVIII strain, halobacterial cells form a more pronounced negative aerotaxis boundary (FIG. 5A, HemAT-Hs+ΔHtrVIII). These cells were repelled from the air/liquid interface much faster and created a denser aerotactic band than the aerotactically wild type or ΔHtrVIII strains containing genomic copy of hemAT-Hs (FIG. 5A, wild type and HemAT-Hs+ΔHtrVIII). The aerophilic response in *B. subtilis* proceeds more rapidly than it does in *H salinarum* (30 versus 180 min) because *B. subtilis* swims faster than *H salinarum*. In the wild-type, an aerotactic band formed at the air interface (Fig. 5B). This band did not form in a strain from which all ten putative MCP-like transducers (Δten) were deleted (FIG. 5B). A strain lacking only HemAT-Bs showed an aerophobic response, indicating the presence of a second, unidentified aerotaxis receptor. To demonstrate the physiological function of HemAT-Bs unequivocally, hemAT-Bs was overexpressed in a strain from which all *B. subtilis* transducer genes were deleted (Δten strain). When HemAT-Bs was overexpressed in the Δten strain, the aerophilic response was observed (FIG. 5b). These assays demonstrate that HemAT-Bs is involved in an aerophilic response in *B. subtilis*.

Example 3

Expression of HemAT-Hs and HemAT-Bs in *Escherichia Coli*

The FAD-binding aerotaxis transducer Aer in *E. coli* has a PAS domain that is similar to the redox-sensing domain of the NifL protein of *Azotobacter vinelandii* (Hill et al., *Proc. Natl Acad Sci. USA*, 93:2143–2148 (1996); Zhulin et al., *Mol. Microbiol.*, 29:1522–1523 (1998), which are hereby incorporated by reference) and FixL from *R. meliloti* (Gilles-Gonzalez et al., *Nature*, 350:170–172 (1991), which is hereby incorporated by reference). FixL is a chimeric membrane protein with a histidine kinase domain, which belongs to the large class of two-component regulatory systems, whereas the heme-binding sensory domain belongs to the PAS domain super family (Gilles-Gonzalez et al., *Nature*, 350:170–172 (1991); Lois et al., *J. Bacteriol.*, 175:1103–1109 (1993); Gong et al., *Proc. Natl. Acad. Sci. USA*, 95:15177–15182 (1998), which are hereby incorporated by reference). None of the PAS domains identified in the genome of *B. subtilis* is present in chemotaxis transducers (Zhulin et al., *Mol. Microbiol.*, 29:1522–23 (1998), which is hereby incorporated by reference). To identify the nature of the prosthetic groups in HemAT-Hs and HemAT-Bs, both proteins were expressed in *E. coli* by constructing vectors, which express the hemAT-Hs or hemAT-Bs gene under the control of an inducible T7 promoter (Studier et al., *Methods in Enzymology*, 185:60–89 (1990), which is hereby incorporated by reference).

Using a combination of anion exchange and gel-filtration chromatography, HemAT-Hs was purified (The BL21 pLysS host cells harboring hemAT-Hs or hemAT-Bs genes were grown to $OD_{600}$=0.4 in 1 L of LB with appropriate antibiotics and induced with 0.6 mM IPTG. The cells were harvested by low speed centrifugation (4000×g) for 15 min. at 4° C. after a two-hour induction. The pellets were resuspended in 50 ml buffer (50 mM NaCl, 50 mM Tris-HCl, pH6.0) and sonicated for a total of 4 minutes (20 second pulses with 30 second pauses). The sonicated solution was centrifuged at 28,000×g for 20 min. The brown red supernatant with HemAT-Hs or HemAT-Bs was used for purification. HemAT-Hs: The supernatant was filtered through 0.2 micron filter and applied to BioCAD anion exchange POROS HQ/M (16/100) perfusion chromatography column equilibrated with 50 mM Tris-HCl, pH6.0. A linear gradient of NaCl (0–1500 mM) was applied and Hem-AT-Hs was eluted at about 400 mM. For further purification, the fractions containing the HemAT-Hs (monitored by Soret band absorbence at 410 nm and SDS-gel electrophoresis) were concentrated and applied to a Hiload Superdex 200 16/60 gel filtration column. Peak fractions were concentrated with an Amicon 100K concentrator and used for spectroscopy. HemAT-Bs: A saturated $(NH_4)_2SO_4$ solution was added to the brown red supernatant to 30% and centrifuged at 28,000×g for 20 min. The optically clear light brown supernatant was further fractionated by $(NH_4)_2SO_4$ addition to 36% saturation followed by centrifugation. The resultant pellet was solubilized in a resuspension buffer (500 mM NaCl, 50 mM Tris-HCl, pH8) and applied to a Hiload 26/60 Superdex 75 gel filtration column. Peak fractions containing HemAT-Bs (monitored by Soret band absorbence at 410 nm and SDS-gel electrophoresis) were concentrated by an Amicon 50K concentrator and used for spectroscopy). Recombinant HemAT-Hs expressed in *E. coli* under low ionic strength conditions was shown to contain a high degree of secondary structure consistent with a predicted folded protein (Larsen et al., *J. Prot. Chem.*, 18(3) (1999), which is hereby incorporated by reference).

The purified HemAT-Hs migrates at a position higher than the calculated 52.8 kDa for the mature protein (FIG. 2B line HemAT-Hs). This slow electrophoretic migration in SDS-polyacrylamide gels is consistent with the highly acidic nature of HemAT-Hs (pI=3.78, 27% acidic residues) and has been observed in other acidic proteins from halophiles (Ihara et al., *Arch. Biochem. Biophys.*, 286:111–116 (1991), which is hereby incorporated by reference). Using a combination of ammonium sulfate precipitation/fractionation and gel filtration chromatography it is possible to purify HemAT-Bs. The BL21 pLysS host cells harboring hemAT-Hs or hemAT-Bs genes were grown to $OD_{600}$=0.4 in 1 L of LB with appropriate antibiotics and induced with 0.6 mM IPTG. The cells were harvested by low speed centrifugation (4000×g) for 15 min. at 4° C. after a two-hour induction. The pellets were resuspended in 50 ml buffer (50 mM NaCl, 50 mM Tris-HCl, pH6.0) and sonicated for a total of 4 minutes (20 second pulses with 30 second pauses). The sonicated solution was centrifuged at 28,000×g for 20 min. The brown red supernatant with HemAT-Hs or HemAT-Bs was used for purification. HemAT-Hs: The supernatant was filtered through 0.2 micron filter and applied to BioCAD anion exchange POROS HQ/M (16/100) perfusion chromatography column equilibrated with 50 mM Tris-HCl, pH6.0. A linear gradient of NaCl (0–1500 mM) was applied and HemAT-Hs was eluted at about 400 mM. For further purification, the fractions containing the HemAT-Hs (monitored by Soret band absorbence at 410 nm and SDS-gel electrophoresis) were concentrated and applied to a Hiload Superdex 200 16/60 gel filtration column. Peak fractions were concentrated with an Amicon 100K concentrator and used for spectroscopy. HemAT-Bs: A saturated $(NH_4)_2SO_4$ solution was added to the brown red supernatant to 30% and centrifuged at 28,000×g for 20 min. The optically clear light brown supernatant was further fractionated by $(NH_4)_2SO_4$ addition to 36% saturation followed by centrifugation. The resultant pellet was solubilized in a resuspension buffer (500 mM NaCl, 50 mM Tris-HCl, pH8) and applied to a Hiload 26/60 Superdex 75 gel filtration column. Peak fractions containing HemAT-Bs (monitored by Soret band absorbence at 410 nm and SDS-gel electrophoresis) were concentrated by an Amicon 50K concentrator and used for spectroscopy). The purified HemAT-Bs migrates in SDS-PAGE as 48.7 kDa protein as expected (FIG. 2, line HemAT-Bs).

Example 4

Absorption Spectra of Purified HemAT-Hs and HemAT-Bs

Figure 4A:
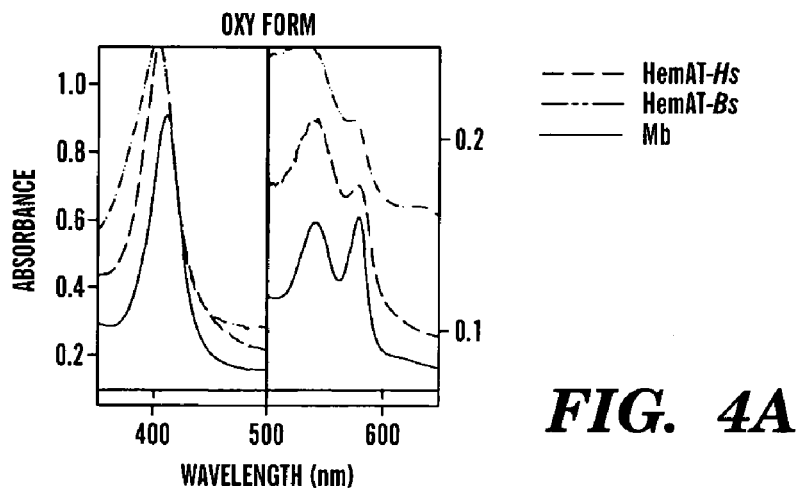
Figure 4B:
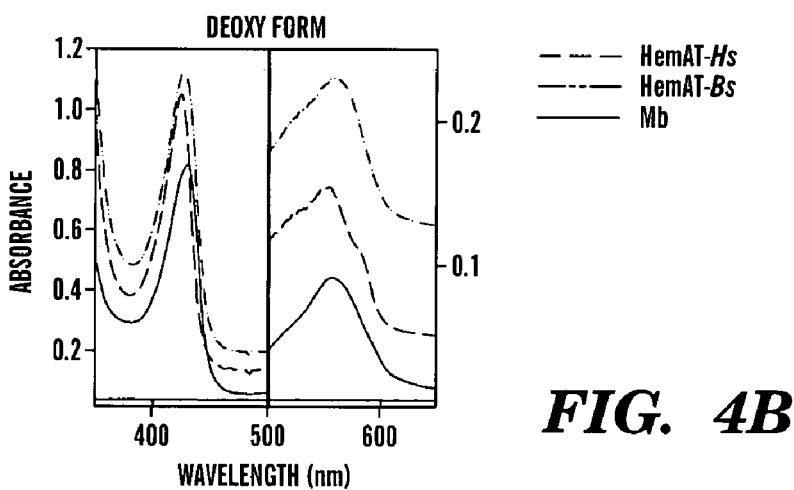
Figure 4C:
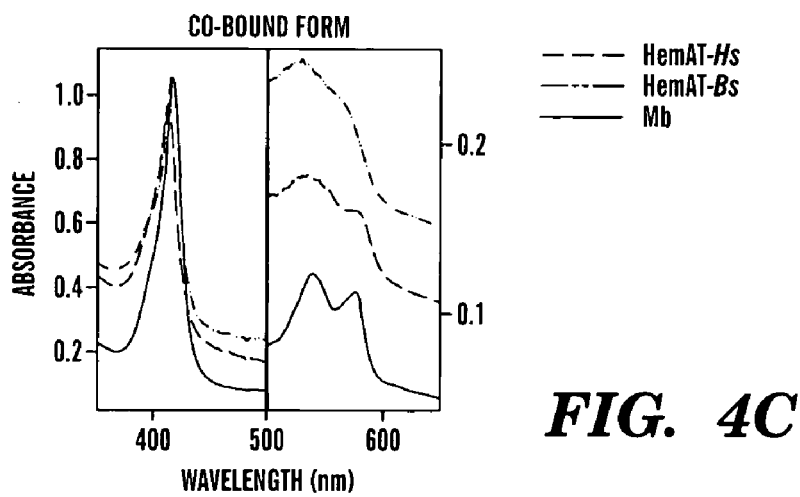

HemAT-Hs and HemAT-Bs display similar absorption spectra in both the near UV and visible regions characteristic of oxygen bound heme proteins. Specifically, absorption band maxima are found at 406 nm (Soret), 578 nm (α-band), and 538 nm (β-band) for both proteins (FIG. 4A). These absorption maxima resemble those of Sperm whale oxymyoglobin (418 nm, 581 nm, and 543 nm) and oxy FixL (415 nm, 577 nm, and 543 nm). Upon deoxygenation (using sodium dithionite), the Soret bands shift to 425 nm while the α- and β-bands converge to a broad band centered at 555 nm, consistent with the formation of a deoxy-form of the protein (i.e., absorption bands for deoxymyoglobin: 434 nm and 556 nm and deoxyFixL: 433 nm and 567 nm) (FIG. 4B). If the deoxy form of HemAT-Hs and HemAT-Bs are exposed to atmospheric oxygen, the absorption spectra revert back to that observed for the purified proteins (FIG. 4D). Both the purified (oxy form) and the deoxy derivatives of HemAT-Hs and HemAT-Bs are reactive towards carbon monoxide. The CO bound derivatives display absorption maxima at 415 nm (Soret), 573 nm (α-band), and 535 nm (β-band) (FIG. 4C). A pyridine hemochrome assay showed the heme group of both HemAT-Hs and HemAT-Bs to be b-type. HemAT-Hs and HemAT-Bs are distinct both in spectral features and in physiological function from the previously discovered heme protein FixL from *R. meliloti* (Gilles-Gonzalez et al., *Nature*, 350:170–172 (1991), which is hereby incorporated by reference). The absorption bands of both HemAT-Hs and HemAT-Bs are blue shifted, relative to FixL, indicating distinct heme pocket geometries. Unlike FixL, HemAT-Hs and HemAT-Bs display no PAS domain sequence homology. In addition, both HemAT-Hs and HemAT-Bs participate in negative aerotaxis while FixL acts as an oxygen sensing kinase.

Example 5

Methylation of HemAT-Hs and HemAT-Bs

It has been postulated that in *E. coli*, adaptation in Aer-mediated aerotaxis is methylation-independent (Taylor et al., *Annu. Rev. Microbiol.*, 53:90–103 (1999), which is hereby incorporated by reference). In contrast to *E. coli*, adaptation during aerotaxis in *H. salinarum* and *B. subtilis* is a methylation-dependent process (Brooun et al., *J. Bacteriol.*, 180:1642–1646 (1998); Lindbeck et al., *Microbiology*, 141:2945–2953 (1995); Wong et al., *J. Bacteriol.*, 177:3985–3991 (1995), which are hereby incorporated by reference). To determine if HemATs can be methylated by the CheR methyltransferase, *H. salinarum* and *B. subtilis* cells were radiolabeled with [methyl-$^3$H] methionine after blocking protein synthesis. The radiolabeled cells were processed for fluorography and immunoblotting with a polyclonal antibody raised against the highly conserved region of methyl-accepting transducers (W. Zhang et al., *Proc. Natl. Acad. Sci. U.S.A.* 93:4649 (1996), which is hereby incorporated by reference). A single radiolabeled band is missing in the ΔhemAT-Hs strain (FIG. 2B, lane 1), whereas this band is present in the overexpression strain (FIG. 2B, lane 2). This band is also recognized by the antibody, suggesting that HemAT-Hs is indeed a methyl-accepting transducer (FIG. 2B, lanes 1' and 2'). In contrast, it was not possible to detect any [methyl-$^3$H]-labeling in HemAT-Bs. Together with the capillary assays, these data demonstrate an important difference in the signaling and adaptation mechanisms for aerotaxis mediated by HemAT-Hs and HemAT-Bs.

Example 6

Materials and Methods for Example 7

PCR and TOPO cloning. C-terminal primers were designed to amplify the 250, 230, 210, 205, 200, 195, 194, 193, 192, 191, 190, 170 and 151 residues of HemAT-Hs and were designed to include BamHI and XbaI restriction sites. The N-terminal primer included EcoRI and NdeI restriction sites. Primer sequences may be found in Table 1. HemAT-Hs genomic plasmid was used as a template for PCR with Pfu polymerase. PCR amplification was performed in a Gene-Amp PCR system 2400 (Perkin-Elmer) under the following conditions: Hot start with Pfu polymerase at 80° C. followed by heat denaturation at 94° C. for 2 minutes was followed by 25 cycles of heat denaturation at 94° C. for 30 seconds, primer annealing at 58° C. for 30 seconds and elongation at 72° C. for 40 seconds. Following the last cycle, samples were maintained at 72° C. for 7 minutes and immediately kept at 4° C. Following PCR, the PCR product was immediately cloned into the TOPO vector (Invitrogen) and transformed into TOP10 competent cells. Clones with the insertion were selected via kanamycin resistance on Luria Bertani (LB) agar plates with kanamycin (50 μg/ml). Colonies were inoculated into CircleGrow (BIO101) with kanamycin media and, following incubation, plasmids were isolated via alkaline mini prep. Plasmids were then restricted with EcoRI to screen for the proper insert.

Cloning into pMAL expression vector. Plasmids containing the correct insert and the expression vector, pMAL-c2, were then digested with EcoRI and BamHI. pMAL-c2 was subsequently dephosphorylated with Alkaline Phosphatase. Digested TOPO plasmids and pMAL plasmid were run on a 1% preparative agarose gel. The truncated hemAT-Hs PCR insert and double digested pMAL-c2 bands were cut from the gel and the DNA was extracted from the gel using the GENECLEAN Spin Kit (BIO101). The hemAT-Hs insert was then ligated to the pMAL-c2 vector at 14° C., overnight. Following ligation, the ligation mixture was transformed into JM109 competent cells. Clones containing the plasmid were selected for by ampicillin resistance on LB agar Amp (100 µg/ml) plates. Ampicillin resistant colonies were inoculated into CircleGrow+Amp media and incubated. Plasmids were isolated via alkaline mini prep and the hemAT-Hs insert was screened for by double digest with EcoRI and BamHI.

Transformation into expression host and protein expression. Plasmids containing the insertion were then transformed into BL21 pLysS competent cells (Novagen). Clones containing both the pMAL-hemAT-Hs insertion plasmid and the pLysS plasmid were screened for by ampicillin (100 µg/ml) and chloramphenicol (34 µg/ml) resistance on LB agar plates. To check for expression of the truncated MBP-HemAT-Hs fusion protein, cells were inoculated into LB Amp and Chl broth and grown to an $OD_{600}$=0.4 followed by induction with 1 mg/ml IPTG. After induction for 1.5 hours, protein samples of uninduced and induced cultures were prepared and run on a 10% SDS-PAGE. This was then followed by staining for protein with Coomasie Blue and destaining with 10% acetic acid.

Protein purification by affinity chromatography and spectral analysis. Cultures which showed induction of the MBP-HemAT-Hs protein were then grown up in a larger scale to $OD_{600}$=0.4 and induced with IPTG (1 mg/ml). Induced cultures were then centrifuged at 5,000 rpm for 20 minutes at 4° C. followed by a wash with column buffer (20 mM Tris-HCl, 200 mM NaCl, 1 mM EDTA) and centrifuged again at 5,000 rpm for 20 minutes at 4° C. If purification did not immediately follow the wash, protein pellets were stored at −70° C. Protein pellets were then resuspended in column buffer, sonicated for 2 minutes (20 second pulses at 45 second intervals) resuspended in column buffer, sonicated for 2 minutes (20 second pulses at 45 second intervals) and centrifuged at 15,000 rpm for 20 minutes at 4° C. The protein containing supernatant was decanted, diluted 1:2 and stored on ice. After setting up the amylose resin column (New England BioLabs), it was washed with 8 column volumes of cold column buffer. The sample was then loaded onto the column at a flow rate of 1 ml/min. followed by a 12 column volume wash with cold column buffer. MBP-HemAT-Hs protein was eluted with 10 mM maltose column buffer and collected in 1 ml fractions. Samples containing the most protein were used to determine the spectra via spectrophotometer. Following elution, a 10% SDS-PAGE was also often run to determine the amount of protein in elutions. Eluted samples were stored at 4° C.

Example 7

Truncated HemAT-Hs

The finding that HemAT-Hs, an archael signal transducer, is a heme binding protein provides a unique opportunity to study not only the physiological function of this protein, but also obtain greater understanding of the structure of this soluble protein and how heme interacts with it. Therefore, this project aims to identify the minimum size of HemAT-Hs to which heme binds. This will be done by truncating the gene, first from the C-terminal, by PCR. Once the minimum size of the functional heme binding domain is found from the C-terminal, the N-terminal will then be truncated to further identify residues crucial in proper heme binding. Producing this truncated HemAT-Hs protein which still retains the functional heme binding domain will aid in efforts to determine HemAT-Hs protein structure.

Analysis of heme binding in HemAT-Hs began with the first 151 residues of HemAT-Hs. However, preliminary spectral analysis showed no heme binding. Primers were then designed to amplify HemAT-Hs every 20 amino acids from 150 thereby amplifying the first 170, 190, 210, 230, and 250 amino acids of the N-terminal. HemAT-Hs 210 showed the spectra of heme bound to HemAT-Hs and also exhibited the characteristic red spectra of $O_2$ bound heme in purified protein samples. HemAT-Hs 190, however, did not present color in protein samples, nor did it have the visible bands at 540 nm and 580 nm which represent bound heme. Primers were then designed every 5 amino acids from 210 to 190 at 205, 200 and 195 to determine more precisely where heme binds. Only 200 and 195 construction fused with MBP showed a reddish color in protein samples along with the characteristic spectra.

This narrowed the search down for the heme binding site to between 195 and 190 amino acids of HemAT-Hs; thus, primers were designed at 191, 192, 193 and 194 amino acids. The spectra for the 192 and 191 constructs shows altered visible bands at 540 nm and 580 nm. The 194 construction shows a similar spectra, like wild-type HemAT-HS or the HemAT-Hs 195 construct.

Example 8

Purification of Recombinant HemAT-Hs by Metal Chelate Chromatography

1 L of *E. coli* culture containing HemAT-Hs was collected, washed with Buffer #2 (200 MM NaCl, 50 mM Sodium

TABLE 3

Names and sequences (5' to 3') of primers used in HemAT-Hs truncation.

| Primer Name | Sequence (5' to 3') | |
|---|---|---|
| hemAT-Hs EcoRI/NdeI top | ccgaattccatatgagcaacgataatgac | SEQ. ID. No. 48 |
| hemAT-Hs 151 BamHI/XbaI bot | ctctagaggatccctagtcgtcggcaagcgcgtcc | SEQ. ID. No. 49 |
| hemAT-Hs 250 B/X bot | cctctagaggatccntagacgtcagccatgcggtc | SEQ. ID. No. 50 |
| hemAT-Hs 230 B/X bot | cctctagaggatccctaggcgacgtcctgcgaggtcgcc | SEQ. ID. No. 51 |
| hemAT-Hs 210 B/X bot | cctctagaggatccctacgcgttcgccaactcctggcggc | SEQ. ID. No. 52 |
| hemAT-Hs 190 B/X bot | cctctagaggatccctagatgtaggtgtccattgcgatc | SEQ. ID. No. 53 |
| hemAT-Hs 170 B/X bot | cctctagaggatccctaccgggccacgagttcgtcgac | SEQ. ID. No. 54 |
| hemAT-Hs 205 B/X bot | cctctagaggatccctactggcggctgtcgatctcgtc | SEQ. ID. No. 55 |
| hemAT-Hs 200 B/X bot | cctctagaggatccctactcgtcgtggaggcgctgggc | SEQ. ID. No. 56 |
| hemAT-Hs 195 B/X bot | cctctagaggatccctactgggcgtacgagtcgatgtag | SEQ. ID. No. 57 |
| hemAT-Hs 194 B/X bot | cctctagaggatccctaggcgtacgagtcgatgtaggtgtcc | SEQ. ID. No. 58 |
| hemAT-Hs 193 B/X bot | cctctagaggatccctagtacgagtcgatgtaggtgtcc | SEQ. ID. No. 59 |
| hemAT-Hs 192 B/X bot | cctctagaggatccctacgagtcgatgtaggtgtccattgcg | SEQ. ID. No. 60 |
| hemAT-Hs 191 B/X bot | cctctagaggatccctagtcgatgtaggtgtccattgcg | SEQ. ID. No. 61 | phosphate, pH 8.0), and resuspended in 40 ml of Buffer #2. Cells are sonicated. Insoluble material is removed by ultracentrifugation at 100,000 rpm for 20 minutes. POROS MC/M (100×1.6 I.D., 20 µm) is used for metal chelate chromatography. The column is washed with 50 mM EDTA, 1 M NaCl, pH 8.0 over 10 column volumes followed by a wash with water. 100 mM $CoCl_2$ is used to charge the column, followed with a wash with 1 M NaCl and water. The column is equilibrated in buffer containing 5 mM imidazole. 5 ml of sample is loaded directly onto the column at a flow rate of 2–4 m/min and a gradient of imidazole from 0–500 mM is run over 30 column volumes at 10 ml/min. Fractions containing recombinant HemAT-Hs is pooled and concentrated using Centricon 50.

Example 9

Site Directed Mutagenesis of HemAT-Hs

In order to perform PCR-based site-directed mutagenesis, a plasmid containing the hemAT-Hs gene to be mutated with proper size has to be constructed first. The proper restriction recognition sites are created by designing the primers with the recognition site tags in the primers as follows:

hemAT-Hs EcoRI/NdeI top primer:
5'CCGAATTCCATATGAGCAACGATAATGAC 3' (SEQ. ID. No. 62)

hemAT-Hs BamHI/XbaI bottom primer:
5'CCTCTAGACTAGCTGAGCTTGCCGACC 3' (SEQ. ID. No. 63)

Two sites in each primer were created to meet the needs of expressing HemAT-Hs in different expression vectors. hemAT-Hs genomic DNA in pDelta vector was used as a template for amplifying hemAT-Hs gene by PCR using proofreading DNA polymerase pfu. PCR product was cloned into TOPO vector (Invitrogen TOPO cloning Kit). The insert was checked and confirmed by digestion and PCR. This construction was used as template for generating serial histidine mutants.

The plasmid construction from above was used for mutagenesis PCR. His 20, His 71, His 123, His 198, and His 214 were mutated to alanine by PCR-based site-directed mutagenesis (described above). Mutated hemAT-Hs gene in Topo vector has been checked by manual sequence as well as Auto Sequencer 373.

Example 10

Expression of Mutated HemAT-Hs

The hemAT-Hs/pTOPO construction was used as initial plasmid for the subcloning of hemAT-Hs gene into different vectors. Three different expression systems were used. First, the pMAL system was used for expression in *E. coli* (Fusion protein expression system). EcoRI and BamHI restriction digestion sites were used for cloning the mutated hemAT-Hs gene into pMAL vector. The protein expressed in this system is a MBP HemAT-Hs fusion protein. All of the mutants have been cloned into pMAL, expressed successfully, purified and spectra have been done as well.

Second, the pET system is also used for expression of the peptides in *E. coli*. NdeI and BamHI restriction digestion sites were used for subcloning hemAT-Hs into pET vector.

Third, in order to study the physiological function of HemAT-Hs in its native host, it has to be expressed in halobacterial ΔhemAT-Hs strain, a strain that hemAT-Hs gene has been deleted from its genome. NdeI and XbaI were used to clone mutated hemAT-Hs gene into a halobacterial shuttle expression vector pKJ427. hemAT-Hs/pTOPO plasmid was digested with NdeI and XbaI, as well as the shuttle vector pKJ427. Digested vector and hemAT-Hs insert were purified from agarose gel by GeneClean kit and ligated with T4 ligase at 4° C. Ligation reaction was transformed into *E. coli* competent cells. Colonies were inoculated, the plasmids were extracted and checked by double digestion and PCR. The final construction was transformed into halobacterial hemAT-Hs deletion strain for over-expressing HemAT-Hs in *H. salinarum* (standard halobacterial transformation protocol was used). Cultures were checked for expression of HemAT-Hs by immunoblot using both HC23 antibody and HemAT-Hs specific antibody. The clone with highest expression of HemAT-Hs was used for physiological study.

Example 11

Construction of a C-Terminal His-Tag of HemcAT-Hs

In order to purify HemAT-Hs protein from its native host *Halobacterium salinarum* C-terminal His-tag was constructed. A two-step PCR strategy was used. First, an NdeI top primer and 20 nucleotide C-terminal of hemAT-Hs gene

TABLE 4

Primers for mutagenesis.

| Primer Name | Sequence | |
|---|---|---|
| H20A | GGAACGGGATCGACGGGgccGCACTCGCGGACCGG | SEQ. ID. No. 64 |
| H20A-R | CCGGTCCGCGAGTGCggcCCCGTCGATCCCGTTCC | SEQ. ID. No. 65 |
| H70A | GACCGACTTCTACGACgccTTGGAGTCCTACGAGCG | SEQ. ID. No. 66 |
| H70A-R | CGCTCGTAGGACTCCAAggcGTCGTAGAAGTCGGTC | SEQ. ID. No. 67 |
| H123A | CCGTATCGGGAAGATAgccGACGTGCTCGGGCTCG | SEQ. ID. No. 68 |
| H123A-R | CGAGCCCGAGCACGTCggcTATCTTCCCGATACGG | SEQ. ID. No. 69 |
| H198A | CGTACGCCCAGCGCCTCgccGACGAGATCGACAGCC | SEQ. ID. No. 70 |
| H198A-R | GGCTGTCGATCTCGTCggcGAGGCGCTGGGCGTACG | SEQ. ID. No. 71 |
| H214A | GCGAACGCGGTCGCCACGgccGTGGAAGCACCGCTG | SEQ. ID. No. 72 |
| H214A-R | CAGCGGTGCTTCCACggcCGTCYGCGACCGCGTTCGC | SEQ. ID. No. 73 |

Total of 10 mutants have been done, including H20A, H70A, H123A, H198A, H214A, H20/70A, H20/123A, H70/123A, $H_{20/70/123}$A.

plus sequence encoding 6-histidine primer were used for amplification. Second, using first round PCR product as template, NdeI top primer and 6-Histidine+Stop codon bottom primer were used for PCR. The primer (including BamHI/XbaI cutting sites) was used to amplify the hemAT-Hs gene plus histidine codon as well as stop Codon right after 6-his sequence. TOPO cloning was used for cloning the PCR products. NdeI/XbaI were used for subcloning of hemAT-Hs-6-His-stop construction into shuttle vector pKJ427. The final construction plasmid was transformed into hemAT-Hs deletion strain.

Example 12

HemAT-Hs Overexpression Construction in *H. Salinarum*

Expression of HemAT-Hs in *Halobacterium salinarum* was created in the expression vector pKJ 427. pKJ 427 plasmid contains a fedox promotor with an mevinolin resistant gene. NdeI and XbaI restriction recognition sites were used to clone the hemAT-Hs gene into the pKJ427 vector. Top primer with NdeI cutting site and bottom primer with XbaI cutting site were designed and used for amplifying hemAT-Hs gene from Halobacterium salinarum genomic DNA by proof-reading pfu DNA polymerase. The PCR product was cloned into TOPO cloning vector (Invitrogen) and transformed into *E. coli* competent cells. The plasmid containing hemAT-Hs gene in TOPO vector was subcloned into pKJ 427 vector by NdeI/XbaI double digestion. The hemAT-Hs/pKJ427 construction was confirmed by PCR as well as NdeI/XbaI double digestion and then, the plasmid was transformed into ΔhtrVIII deletion strain using standard transformation protocol. After two week incubation, colonies were picked up and grown in halobacterial growth medium. Each individual culture was checked by PCR to confirm the presence of the plasmid, and by immunoblot to confirm the expression level of HemAT-Hs.

Example 13

Expression of HemAT-Bs

As with hemAT-Hs, three expression systems have been developed. First, hemAT-Bs is expressed in the pMAL expression system. In order to express hemAT-Bs encoding protein HemAT-Bs in *E. coli*, expression primers were needed to amplify the hemAT-Bs gene. Not only the gene, but the ribosomal binding region upstream of the start codon, is required for the expression of HemAT-Bs in *E. coli*.

BamHI and PstI were selected for the cloning of hemAT-Bs into expression vector and *E. coli-Bacillus subtilis* shuttle vector. hemAT-BsBamHI top/PstI bot primers were used to amplify the hemAT-Bs gene from *Bacilus subtilis* genomic DNA by PCR with pfu DNA polymerase. After PCR, the amplicon was immediately cloned into TOPO vector using invitrogen TOPO Blunt Cloning kit and transformed into TOP 10 *E. coli* competent cells. Colonies were checked for the right insert.

BamHI and PstI were also used for the cloning of the HemAT-Bs into pMAL cII vector as well as the shuttle vector pEB 112. hemAT-Bs/pMAL construction was transformed to *E. coli* pLysS cells for the expression. After IPTG induction, SDS gel showed two bands in comparison to the uninduced sample. The top band is HemAT-Bs protein. The spectra is checked and the results showed clearly the heme-protein signature peaks while the MBP itself doesn't show any peak at 410 nm and 541 nm/580 nm.)

Second, the NdeI top and BamHI bot primers were used for the cloning of hemAT-Bs gene into pET vector. The ribosomal binding region is also included in front of the gene. TOPO cloning was performed after PCR reaction and the construction was confirmed by NdeI/BamHI digestion as well as PCR. hemAT-Bs/pET construction was transformed into *E. coli* pLysS competent cells. IPTG was used for the protein induction. Spectra showed the specific peaks for hemeprotein.

A peptide consisting of the N-terminal 190 or 250 residues was expressed in pMAL vector. A bottom primer at position 190 and 250 amino acid residue were synthesized with a PstI cutting site. hemAT-Bs BamHI top and these top primers were used to amplify the gene encoding 190 and 250 amino acids at N-terminal of hemAT-Bs. The PCR products were cloned into TOPO vector and then subcloned into pMAL HemAT-Bs 250 vector by using BamHI/PstI. 190 and 250 hemAT-Bs/pMAL constructions were confirmed and transformed into pLysS cells for expression. As expected, other than MBP, a second protein band appears at position 25 and 30 kDa, which are the sizes of N-terminal 190 and 250 residues of HemAT-Bs protein. Spectra also showed the signature peaks of hemeprotein.

A shuttle vector is used for the expression of hemAT-Bs gene in its native host *B. subtilis*. hemAT-Bs/TOPO construction was used as initial plasmid. The hemAT-Bs/pEB 112 construction was transformed into ΔhemAT-Bs deletion strain. The transformant was used for physiological study of HemAT-Bs.

Example 14

Construction of a C-terminal His-Tag HemAT-Bs

Two round of pfu PCR were performed to generate a C-terminal 6 His-tag to HemAT-Bs. The top primer and

TABLE 5

Primers for PCR or HemAT-BS.

| Name of Primer | Sequence |
|---|---|
| hemAT-Bs BamHItop | ATATGGATCCAAGGGGGATCATTGTAATGTTATTTAAAAAAG SEQ. ID. No. 74 |
| hemAT-Bs PstIbot | ATTACTGCAGCAACTGATTTTTAATTTAAGTTTACATAATGAACGC SEQ. ID. No. 75 | bottom primer with 6 Histidine codon plus stop codon were used for the first round PCR. The PCR product was cloned into TOPO vector and the resultant vector used for the second round PCR. In the case of pET, NdeI and BamHI sites were created to clone the insert into expression vector. In the case of pMAL, BamHI top and BamHI bot primer were used. The final constructions (pET/pMAL) were transformed to *E. coli* pLysS cells for induction.

Example 15

Site-Directed Mutagenesis of HemAT-Bs

The same strategy is used for generating site-directed mutants for HemAT-Bs of *B. subtilis*. The HemAT-Bs/TOPO construction with BamHI top and PstI bottom restriction sites was used as template for PCR-based mutagenesis. HemAT-Bs H75A, H86A, H99A, H122A, H123A and H199A are being mutated by PCR-based mutagenesis. The HemAT-Bs/pTOPO plasmid was used as initial template for PCR.

The mutants, H75A, H99A, and H123A, have been cloned into pMAL expression vector. H123A spectra showed no significant signature peaks at 540 nm and 580 nm. H123R from pMAL expression culture showed no hemeprotein signature spectra.

Example 16

Carbon Monoxide Binding in HemAT-Hs and HemAT-Bs

The rate of CO binding to both HemAT-Hs and HemAT-Bs was determined by transient absorption spectroscopy using instrumentation described previously (Larsen, et al., *Inorg. Chim. Acta* 234:101–107(1995), which is hereby incorporated by reference).

The rates of CO dissociation for HemAT-Hs and HemAT-Bs were determined using the ferricyanide method (Gilles-Gonzalez, et al., *Biochemistry* 33:8067–8073 (1994), which is hereby incorporated by reference). Changes in absorbance as a function of time at 418 nm (Soret maximum for the CO bound derivative of each protein) were monitored after the addition of potassium ferricyanide (final concentration of 1.5 mM) to solutions of the co-bound protein. The resulting traces were then fit to single exponential decays to obtain $k_{off}$ assuming the following reaction:

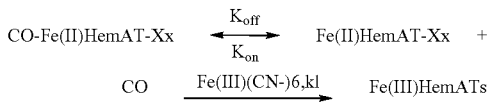

where $k_{off}/k_{on}$ are the dissociation/association rate constants and k1 is the rate of HemATs oxidation. This procedure relies on k1 being much larger than $k_{off}$. In the case of the HemATs proteins this was confirmed by measuring the rate of heme oxidation of the five-coordinate deoxy form the protein.

The optical absorption spectrum of deoxy and CO-bound derivatives of HemAT-Hs and HemAT-Bs are shown in FIG. 4. The absorption spectra of the deoxy forms of both proteins are indicative of five-coordinate high-spin heme with Soret maxima at 425 nm and a broad visible band centered at 555 nm. In the presence of CO the absorption spectrum resembles a six-coordinate low-spin heme with a Soret maximum at ~418 nm (HemAT-Hs/Bs) and visible bands at 535 nm and 573 nm.

FIG. 6 displays typical transient absorption data subsequent to CO photolysis obtained at 430 nm at 25° C. and 1 atm CO for both HemAT-Hs (solid line) and HemAT-Bs (dotted line). The data can be fit to a single exponential decay indicating a pseudo-first order reaction with CO. The resulting rate constant for CO recombination are found to be 30±3 $s^{-1}$ and 132±3 $s^{-1}$ for HemAT-Hs and HemAT-Bs, respectively. FIGS. 7A–B show the corresponding transient difference spectrum (25 µs subsequent to photolysis) overlaid with the equilibrium difference spectrum (deoxy minus CO-bound) for HemAT-Hs (FIG. 7A, top panel) and HemAT-Bs (FIG. 7B, bottom panel). The red-shift in the transient difference spectra relative to the equilibrium difference spectra suggest that CO photolysis produces a non-equilibrium five-coordinate complex within 25 µs subsequent to photolysis.

Figure 8:
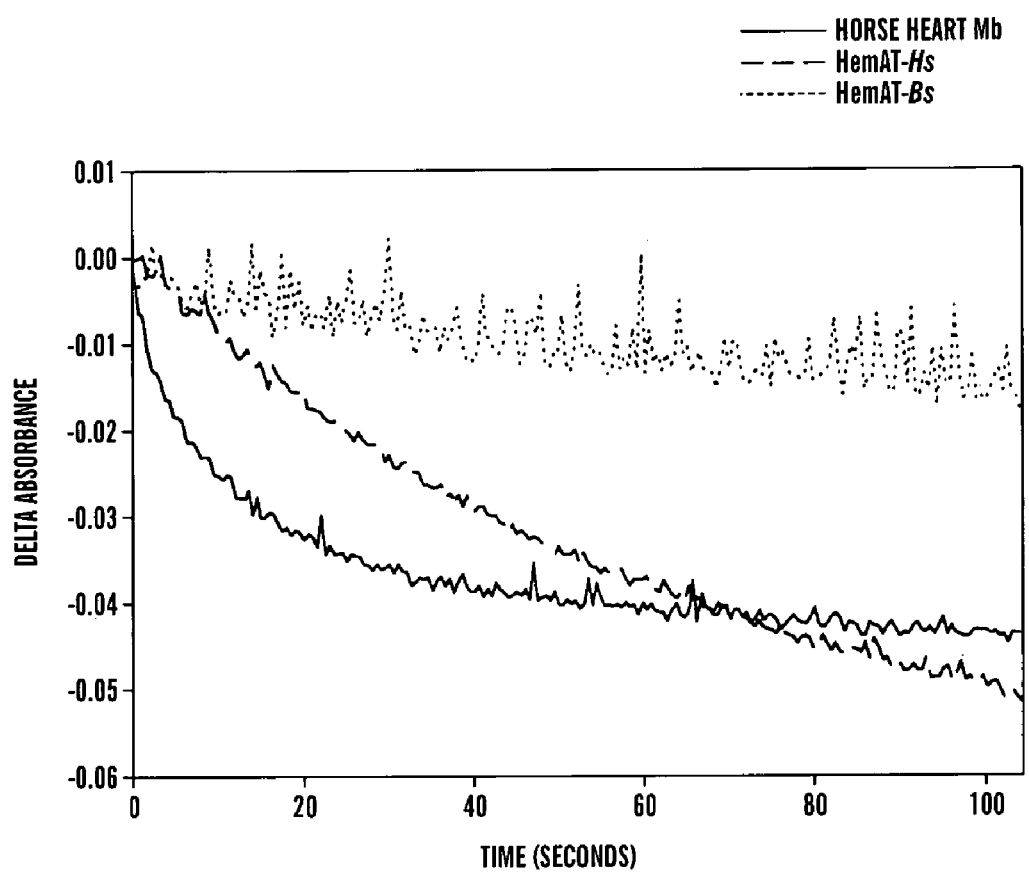

FIG. 8 displays the CO-off rate data for HemAT-Hs, HemAT-Bs, and horse heart Mb. The CO off-rates are found to be 0.2±0.01 $s^{-1}$, 0.098±0.002 $s^{-1}$, and 0.056±0.001 $s^{-1}$ for HemAT-Hs, HemAT-Bs, and horse heart Mb, respectively. Using these values along with the second-order rate constants for CO recombination (scaling the pseudo first order rate constants to CO concentration) the associations constants for CO are found to be 1.5×10$^4$ M$^{-1}$, 1.35×10$^6$ M$^{-1}$, and 7.38×10$^6$ M$^{-1}$ for HemAT-Hs, HemAT-Bs, and horse heart Mb, respectively. These values along with literature values for CO binding to other heme proteins are provided in Table 6.

TABLE 6

CO-Affinities of various heme proteins.

| Protein | K (×10$^{-4}$M$^{-1}$) | K$_{on}$ (×10$^{-4}$M$^{-1}$s$^{-1}$) | K$_{off}$ (s$^{-1}$) |
|---|---|---|---|
| HemAT-Hs[a] | 15 | 3 | 0.2 |
| HemAT-Bs[a] | 135 | 13.2 | 0.098 |
| HH Mb[a] | 738 | 46.5 | 0.06 |
| SW Mb[b] | 2700 | 51 | 0.019 |
| SW Mb H(E7)->L[b] | 110,000 | 2,600 | 0.024 |
| Human HbA[c] | 50,000 | 600 | 0.013 |
| BjFixL[c] | 10 | 0.5 | 0.045 |
| RmFixLT[c] | — | 1.2 | — |
| RmFixLH[c] | 20 | 1.7 | 0.083 |
| HRP (pH 7.0)[c] | 350 | 0.3 | 0.0001 |
| Aplaysia Mb[c] | 3,000 | 50 | 0.02 |

[a]This work.
[b]Springer, et al., Chem. Rev. 94:699–714 (1994), which is hereby incorporated by reference.
[c]Gilles-Gonzalez, et al., Biochemistry 33:8067–8073 (1994), which is hereby incorporated by reference.

The absorption spectra of oxy-, deoxy-, and carbon monoxide forms of HemAT-Hs and HemAT-Bs establish that both proteins have a heme prosthetic group to reversibly bind oxygen. Capillary assays demonstrate that both HemAT-Hs and HemAT-Bs are involved in negative aerotaxis in phylogenetically distinct archaeon *H. salinarum* and gram-positive bacterium *B. subtilis*, respectively. Thus, the N-terminal segments of HemAT-Hs and HemAT-Bs may act as sensory domains by binding diatomic oxygen through the heme prosthetic group in the ferrous (Fe(II)) state. This oxygen binding triggers a conformational change in the sensor domain, which in turn alters the activity of the C-terminal signaling domain. This initiates association of the signaling domain with CheW and CheA proteins to generate signals that change the flagellar rotational bias.

Current evolutionary reconstruction indicates that myoglobin, (α- and β-globins derive from a protein that originally appeared in an ancient vertebrate about 500 million years ago (Hardison, *Amer. Scientist,* 87:126–137 (1999), which is hereby incorporated by reference). However, comparison of amino acid sequences in globins from Eukarya and Bacteria suggests they share a very early common ancestor, in spite of the fact that the proteins perform different functions (Hardison, *Amer. Scientist*, 87:126–137 (1999); Hardison, *J. Exp. Biol.*, 201:1099–1117 (1998), which are hereby incorporated by reference). The conserved residues among all myoglobins are the proximal histidine residue in the F helix (F8) and two phenylalanine residues in the CD region (CD1 packs against the heme and CD4 in a hydrophobic cluster in contact with the heme), the distal histidine residue in the E helix (E7) and a proline residue at the beginning of the C helix (C2, sharp turn between B and C helices) (Bashford et al., *J. Mol. Biol.*, 196:199–216 (1987); Vinogradov et al., *Comp. Biochem. Physiol.*, 106B: 1–26 (1993), which are hereby incorporated by reference). Three of these residues (proline in C2, phenylalanine in CD4 and histidine in F8) are conserved and phenylalanine in CD1 is replaced by valine in HemAT-Hs and HemAT-Bs (marked with asterisks in FIG. 1A).

HemAT proteins constitute a new class of sensors that differ significantly from the known heme-containing $O_2$-sensor FixL (16, 17). FixL is a member of the large family of sensor kinases ubiquitous in bacterial two-component regulatory systems. Its heme-binding domain belongs to the PAS-domain superfamily (18, 19). HemATs contain no PAS domains (Taylor, et al., *Ann. Rev. Microbiol.*, 53:90 (1999); Zhulin et al., *Mol. Microbiol.*, 29:1522 (1998), which are hereby incorporated by reference) and differ from FixL both in spectral features and physiological function (Gilles-Gonzalez, et al., *Nature*, 350:170 (1991); Lois, et al., *J. Bacteriol.*, 175:1103 (1993), which are hereby incorporated by reference). The absorption bands of HemATs are blue-shifted relative to FixL (415 nm Soret band), indicating that the proteins have distinct heme-pocket geometries. In addition, both HemATs participate in aerotaxis, whereas FixL regulates transcription. HemATs also differ from the aerotaxis transducer Aer in *E. coli*, which has a FAD-binding PAS domain (Rebbapragada et al., *Proc. Natl. Acad. Sci. U.S.A.*, 94:10541 (1997); Bibikov et al., *J. Bacteriol.*, 179: 4075 (1997), which are hereby incorporated by reference).

The amino-terminal domains of HemATs are proposed to act as sensors by binding diatomic oxygen at their heme when it is in the ferrous (Fe [II]) state. Oxygen binding presumably triggers a conformational change in the sensor domain that, in turn, alters the activity of the carboxyl-terminal signaling domain. The carboxyl-terminal domains of HemATs are very similar to the signaling domains of the MCP family of bacterial chemoreceptors, which associate with the cytoplasmic CheW and CheA proteins to mediate chemotaxis.

HemATs offer the possibility of being used as biological sensors to monitor physiologically important gases, such as O2 or CO, because: 1) they are soluble proteins like myoglobin, which has been widely studied at the molecular level; 2) they possess a signaling domain that resembles those of the molecularly well-characterized bacterial chemotaxis transducers; and 3) direct observation of the aerotactic response permits rapid analysis of various perturbations of the sensing and signaling system. In addition, these two proteins provide information about the evolutionary origins of globins in the Eucarya, Archaea, and Bacteria.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An isolated complex comprising:
a heme binding protein complexed with a heme molecule, wherein said complex reversibly binds oxygen with a low affinity and wherein said protein comprises the amino acid sequence of SEQ ID NO:2.

2. A blood substitute comprising the complex according to claim 1.

3. The complex according to claim 1 wherein the complex is purified.

4. The complex according to claim 1 wherein the complex is recombinant.

5. The complex according to claim 1, wherein the heme molecule is a b-type heme molecule.

6. The complex according to claim 1, wherein the complex has an oxygenated form characterized as having spectral properties of: Soret band absorption at 406 nm, α-band absorption at 578 nm, and β-band absorption at 538 nm.

7. The complex according to claim 1, wherein the complex has a deoxygenated form characterized as having spectral properties of: Soret band absorption at 425 nm, and converged α-band and β-band absorption centered at 555 nm.

8. The complex according to claim 1, wherein the heme binding protein having the amino acid sequence of SEQ ID NO:2 comprises a heme-binding domain that associates with a heme molecule and an aerotaxis signaling domain.

* * * * *

SEQUENCE LISTING

<160> NUMBER OF SEQ ID NOS: 86

<210> SEQ ID NO 1
<211> LENGTH: 1470
<212> TYPE: DNA
<213> ORGANISM: Halobacterium salinarum

<400> SEQUENCE: 1

```
atgagcaacg ataatgacac tctcgtgacc gccgacgttc ggaacgggat cgacgggcac      60
gcactcgcgg accggatcgg cctcgacgag gcggagatcg cgtggcggct gtcgttcacc     120
gggatcgacg acgacacgat ggccgcgctc gccgccgaac agccgctgtt cgaagccacc     180
gcggacgcgc tggtgaccga cttctacgac cacttggagt cctacgagcg cacacaggac     240
ctcttcgcga actccacgaa gaccgtcgag caactcaaag agacgcaggc cgagtacttg     300
ctgggcctcg ggcgcggcga gtacgacacc gagtacgccc ccagcgcgc ccgtatcggg      360 aagatacacg acgtgctcgg gctcggaccg gacgtctatc tgggcgcgta cacgcgatac     420
tacacggggc tgttggacgc gcttgccgac gacgtggtcg ccgaccgcgg cgaggaggcg     480
gccgccgccg tcgacgaact cgtggcccgg ttcctgccga tgttgaagct gttgaccttc     540
gatcagcaga tcgcaatgga cacctacatc gactcgtacg cccagcgcct ccacgacgag     600
atcgacagcc gccaggagtt ggcgaacgcg gtcgccacgc acgtggaagc accgctgtcc     660
tcgctggagg cgacctcgca ggacgtcgcc gagcgcacgg acacgatgcg ggcccgcacc     720
gacgaccagg tcgaccgcat ggctgacgtc agccgtgaga tatccagcgt gtccgcgagc     780
```

```
gtcgaggagg tcgcctcgac ggccgacgac gtccgccgga ccagcgagga cgccgaggcg    840
ctggcccagc agggcgaggc ggccgccgac gacgcgctcg ccacgatgac cgacatcgac    900
gaggcgaccg acggcgtcac cgcgggcgtc gaacagctcg gcgagcgcgc cgccgacgtc    960
gaatcagtga ccggcgtgat cgacgacatc gccgagcaga cgaacatgct ggcgctgaac   1020
gcgtccatcg aggccgcccg cgccggggag gcgggcgagg ggtttgcggt cgtcgccgac   1080
gaggtcaagg ccctcgccga ggagtcccgc gagcagtcca cgcgcgtcga ggagctcgtc   1140
gagcagatgc aggcggagac cgaggagacg gtcgaccagt tggacgaggt caaccagcgc   1200
atcggcgagg gcgtcgagcg cgtcgaggag gcgatggaga ccctccagga gatcaccgac   1260
gccgtcgagg acgccgcaag cgggatgcag gaggtgtcga cggcgaccga cgaacaggcg   1320
gtgagcaccg aggaggtcgc cgagatggtc gacggtgtcg acgaccgcgc gggcgagatc   1380
gcggccgccc tcgatgacat cgccgacgcg accgatcagc aggtccggac cgtcgaggag   1440
gtccgcgaga cggtcggcaa gctcagctag                                    1470
```

<210> SEQ ID NO 2  
<211> LENGTH: 489  
<212> TYPE: PRT  
<213> ORGANISM: Halobacterium salinarum

<400> SEQUENCE: 2

```
Met Ser Asn Asp Asn Asp Thr Leu Val Thr Ala Asp Val Arg Asn Gly
  1               5                  10                  15

Ile Asp Gly His Ala Leu Ala Asp Arg Ile Gly Leu Asp Glu Ala Glu
             20                  25                  30

Ile Ala Trp Arg Leu Ser Phe Thr Gly Ile Asp Asp Thr Met Ala
         35                  40                  45

Ala Leu Ala Ala Glu Gln Pro Leu Phe Glu Ala Thr Ala Asp Ala Leu
     50                  55                  60

Val Thr Asp Phe Tyr Asp His Leu Glu Ser Tyr Glu Arg Thr Gln Asp
 65                  70                  75                  80

Leu Phe Ala Asn Ser Thr Lys Thr Val Glu Gln Leu Lys Glu Thr Gln
                 85                  90                  95

Ala Glu Tyr Leu Leu Gly Leu Gly Arg Gly Glu Tyr Asp Thr Glu Tyr
            100                 105                 110

Ala Ala Gln Arg Ala Arg Ile Gly Lys Ile His Asp Val Leu Gly Leu
        115                 120                 125

Gly Pro Asp Val Tyr Leu Gly Ala Tyr Thr Arg Tyr Tyr Thr Gly Leu
    130                 135                 140

Leu Asp Ala Leu Ala Asp Asp Val Val Ala Asp Arg Gly Glu Glu Ala
145                 150                 155                 160

Ala Ala Ala Val Asp Glu Leu Val Ala Arg Phe Leu Pro Met Leu Lys
                165                 170                 175

Leu Leu Thr Phe Asp Gln Gln Ile Ala Met Asp Thr Tyr Ile Asp Ser
            180                 185                 190

Tyr Ala Gln Arg Leu His Asp Glu Ile Asp Ser Arg Gln Glu Leu Ala
        195                 200                 205

Asn Ala Val Ala Thr His Val Glu Ala Pro Leu Ser Ser Leu Glu Ala
    210                 215                 220

Thr Ser Gln Asp Val Ala Glu Arg Thr Asp Thr Met Arg Ala Arg Thr
225                 230                 235                 240

Asp Asp Gln Val Asp Arg Met Ala Asp Val Ser Arg Glu Ile Ser Ser
                245                 250                 255
```

```
Val Ser Ala Ser Val Glu Glu Val Ala Ser Thr Ala Asp Asp Val Arg
            260                 265                 270

Arg Thr Ser Glu Asp Ala Glu Ala Leu Ala Gln Gln Gly Glu Ala Ala
        275                 280                 285

Ala Asp Asp Ala Leu Ala Thr Met Thr Asp Ile Asp Glu Ala Thr Asp
    290                 295                 300

Gly Val Thr Ala Gly Val Glu Gln Leu Gly Glu Arg Ala Ala Asp Val
305                 310                 315                 320

Glu Ser Val Thr Gly Val Ile Asp Asp Ile Ala Glu Gln Thr Asn Met
                325                 330                 335

Leu Ala Leu Asn Ala Ser Ile Glu Ala Ala Arg Ala Gly Glu Ala Gly
            340                 345                 350

Glu Gly Phe Ala Val Val Ala Asp Glu Val Lys Ala Leu Ala Glu Glu
        355                 360                 365

Ser Arg Glu Gln Ser Thr Arg Val Glu Glu Leu Val Glu Gln Met Gln
    370                 375                 380

Ala Glu Thr Glu Glu Thr Val Asp Gln Leu Asp Glu Val Asn Gln Arg
385                 390                 395                 400

Ile Gly Glu Gly Val Glu Arg Val Glu Glu Ala Met Glu Thr Leu Gln
                405                 410                 415

Glu Ile Thr Asp Ala Val Glu Asp Ala Ala Ser Gly Met Gln Glu Val
            420                 425                 430

Ser Thr Ala Thr Asp Glu Gln Ala Val Ser Thr Glu Glu Val Ala Glu
        435                 440                 445

Met Val Asp Gly Val Asp Asp Arg Ala Gly Glu Ile Ala Ala Ala Leu
    450                 455                 460

Asp Asp Ile Ala Asp Ala Thr Asp Gln Gln Val Arg Thr Val Glu Glu
465                 470                 475                 480

Val Arg Glu Thr Val Gly Lys Leu Ser
                485
```

<210> SEQ ID NO 3
<211> LENGTH: 1390
<212> TYPE: DNA
<213> ORGANISM: Bacillus subtilis

<400> SEQUENCE: 3

| | | | | | |
|---|---|---|---|---|---|
| atgttattta | aaaagacag | aaacaagaa | acagcttact | tttcagattc | aaacggacaa | 60 |
| caaaaaaacc | gcattcagct | cacaaacaaa | catgcagatg | tcaaaaaaca | gctcaaaatg | 120 |
| gtcaggttgg | gagatgctga | gctttatgtg | ttagagcagc | ttcagccact | cattcaagaa | 180 |
| aatatcgtaa | atatcgtcga | tgcgttttat | aaaaaccttg | accatgaaag | ctcattgatg | 240 |
| gatatcatta | atgatcacag | ctcagttgac | cgcttaaaac | aaacgttaaa | acggcatatt | 300 |
| caggaaatgt | ttgcaggcgt | tatcgatgat | gaatttattg | aaaagcgtaa | ccgaatcgcc | 360 |
| tccatccatt | taagaatcgg | ccttttgcca | aaatggtata | tgggtgcgtt | tcaagagctc | 420 |
| cttttgtcaa | tgattgacat | ttatgaagcg | tccattacaa | atcagcaaga | actgctaaaa | 480 |
| gccattaaag | caacaacaaa | atcttgaac | ttagaacagc | agcttgtcct | tgaagcgttt | 540 |
| caaagcgagt | acaaccagac | ccgtgatgaa | caagaagaaa | agaaaaacct | tcttcatcag | 600 |
| aaaattcaag | aaacctctgg | atcgattgcc | attctgtttt | cagaaacaag | cagatcagtt | 660 |
| caagagcttg | tggacaaatc | tgaaggcatt | tctcaagcat | ccaaagccgg | cactgtaaca | 720 |
| tccagcactg | ttgaagaaaa | gtcgatcggc | ggaaaaaaag | agctagaagt | ccagcaaaaa | 780 |

-continued

```
cagatgaaca aaattgacac aagccttgtc caaatcgaaa agaaatggt caagctggat      840
gaaatcgcgc agcaaattga aaaatcttc ggcatcgtca caggcatagc tgaacaaaca      900
aaccttctct cgctcaatgc atctattgaa tccgcccgcg ccggagaaca cggcaaaggc     960
tttgctgtcg tggcaaatga agtgcggaag ctttctgagg atacgaaaaa aaccgtctct   1020
actgtttctg agcttgtgaa caatacgaat acacaaatca acattgtatc caagcatatc   1080
aaagacgtga atgagctagt cagcgaaagt aaagaaaaaa tgacgcaaat taaccgctta   1140
ttcgatgaaa tcgtccacag catgaaaatc agcaaagagc aatcaggcaa atcgacgtc    1200
gatctgcaag ccttcttgg agggcttcag gaagtcagcc gcgccgtttc ccatgtggcc    1260
gcttccgttg attcgcttgt catcctgaca gaagaataac catcaaaaac cggtctgcca    1320
tacggccggt ttttttgcgt tcattatgta aacttaaatt aaaaatcagt tgacataata   1380
attacctgca                                                          1390
```

<210> SEQ ID NO 4
<211> LENGTH: 432
<212> TYPE: PRT
<213> ORGANISM: Bacillus subtilis

<400> SEQUENCE: 4

```
Met Leu Phe Lys Lys Asp Arg Lys Gln Glu Thr Ala Tyr Phe Ser Asp
 1               5                  10                  15

Ser Asn Gly Gln Gln Lys Asn Arg Ile Gln Leu Thr Asn Lys His Ala
            20                  25                  30

Asp Val Lys Lys Gln Leu Lys Met Val Arg Leu Gly Asp Ala Glu Leu
        35                  40                  45

Tyr Val Leu Glu Gln Leu Gln Pro Leu Ile Gln Glu Asn Ile Val Asn
    50                  55                  60

Ile Val Asp Ala Phe Tyr Lys Asn Leu Asp His Glu Ser Ser Leu Met
65                  70                  75                  80

Asp Ile Ile Asn Asp His Ser Ser Val Asp Arg Leu Lys Gln Thr Leu
                85                  90                  95

Lys Arg His Ile Gln Glu Met Phe Ala Gly Val Ile Asp Asp Glu Phe
            100                 105                 110

Ile Glu Lys Arg Asn Arg Ile Ala Ser Ile His Leu Arg Ile Gly Leu
        115                 120                 125

Leu Pro Lys Trp Tyr Met Gly Ala Phe Gln Glu Leu Leu Leu Ser Met
    130                 135                 140

Ile Asp Ile Tyr Glu Ala Ser Ile Thr Asn Gln Gln Glu Leu Leu Lys
145                 150                 155                 160

Ala Ile Lys Ala Thr Thr Lys Ile Leu Asn Leu Glu Gln Gln Leu Val
                165                 170                 175

Leu Glu Ala Phe Gln Ser Glu Tyr Asn Gln Thr Arg Asp Glu Gln Glu
            180                 185                 190

Glu Lys Lys Asn Leu Leu His Gln Lys Ile Gln Glu Thr Ser Gly Ser
        195                 200                 205

Ile Ala Asn Leu Phe Ser Glu Thr Ser Arg Ser Val Gln Glu Leu Val
    210                 215                 220

Asp Lys Ser Glu Gly Ile Ser Gln Ala Ser Lys Ala Gly Thr Val Thr
225                 230                 235                 240

Ser Ser Thr Val Glu Glu Lys Ser Ile Gly Gly Lys Lys Glu Leu Glu
                245                 250                 255
```

```
Val Gln Gln Lys Gln Met Asn Lys Ile Asp Thr Ser Leu Val Gln Ile
            260                 265                 270

Glu Lys Glu Met Val Lys Leu Asp Glu Ile Ala Gln Ile Glu Lys
        275                 280                 285

Ile Phe Gly Ile Val Thr Gly Ile Ala Glu Gln Thr Asn Leu Leu Ser
290                 295                 300

Leu Asn Ala Ser Ile Glu Ser Ala Arg Ala Gly Glu His Gly Lys Gly
305                 310                 315                 320

Phe Ala Val Val Ala Asn Glu Val Arg Lys Leu Ser Glu Asp Thr Lys
                325                 330                 335

Lys Thr Val Ser Thr Val Ser Glu Leu Val Asn Thr Asn Thr Gln
            340                 345                 350

Ile Asn Ile Val Ser Lys His Ile Lys Asp Val Asn Glu Leu Val Ser
                355                 360                 365

Glu Ser Lys Glu Lys Met Thr Gln Ile Asn Arg Leu Phe Asp Glu Ile
370                 375                 380

Val His Ser Met Lys Ile Ser Lys Glu Gln Ser Gly Lys Ile Asp Val
385                 390                 395                 400

Asp Leu Gln Ala Phe Leu Gly Gly Leu Gln Glu Val Ser Arg Ala Val
                405                 410                 415

Ser His Val Ala Ala Ser Val Asp Ser Leu Val Ile Leu Thr Glu Glu
                420                 425                 430
```

<210> SEQ ID NO 5
<211> LENGTH: 57
<212> TYPE: PRT
<213> ORGANISM: Artificial Sequence
<220> FEATURE:
<223> OTHER INFORMATION: Description of Artificial Sequence: Template
      sequence
<221> NAME/KEY: UNSURE
<222> LOCATION: (4)..(57)
<223> OTHER INFORMATION: Xaa at positions 4, 10, 14, 15, 27, and 41-57
      is unknown

<400> SEQUENCE: 5

```
Ile Ile Lys Xaa Thr Val Pro Val Leu Xaa Glu His Gly Xaa Xaa Ile
1               5                   10                  15

Gly Gln Asp Val Leu Val Val Leu Ile Lys Xaa Asn Pro Glu Ile Gln
            20                  25                  30

Glu Lys Phe Phe Phe Phe Lys His Xaa Xaa Xaa Xaa Xaa Xaa Xaa Xaa
        35                  40                  45

Xaa Xaa Xaa Xaa Xaa Xaa Xaa Xaa Xaa
    50                  55
```

<210> SEQ ID NO 6
<211> LENGTH: 55
<212> TYPE: PRT
<213> ORGANISM: Erwinia chrysanthemi

<400> SEQUENCE: 6

```
Ile Lys Ser Thr Ile Pro Leu Leu Ala Glu Thr Gly Pro Ala Leu Thr
1               5                   10                  15

Ala His Phe Tyr Gln Arg Met Phe His His Asn Pro Glu Leu Lys Asp
            20                  25                  30

Ile Phe Asn Met Ser Asn Gln Arg Asn Gly Asp Gln Arg Glu Ala Leu
        35                  40                  45

Phe Asn Ala Ile Cys Ala Tyr
    50                  55
```

```
<210> SEQ ID NO 7
<211> LENGTH: 56
<212> TYPE: PRT
<213> ORGANISM: Vitreoscilla stercoraria

<400> SEQUENCE: 7

Ile Ile Lys Ala Thr Val Pro Val Leu Lys Glu His Gly Val Thr Ile
 1               5                  10                  15

Thr Thr Thr Phe Tyr Lys Asn Leu Phe Ala Lys His Pro Glu Val Arg
            20                  25                  30

Pro Leu Phe Asp Met Gly Arg Gln Glu Ser Leu Glu Gln Pro Lys Ala
        35                  40                  45

Leu Ala Met Thr Val Leu Ala Ala
    50                  55

<210> SEQ ID NO 8
<211> LENGTH: 55
<212> TYPE: PRT
<213> ORGANISM: Escherichia coli

<400> SEQUENCE: 8

Val Lys Ala Thr Ile Pro Leu Leu Val Glu Thr Gly Pro Lys Leu Thr
 1               5                  10                  15

Ala His Phe Tyr Asp Arg Met Phe Thr His Asn Pro Glu Leu Lys Glu
            20                  25                  30

Ile Phe Asn Met Ser Asn Gln Arg Asn Gly Asp Gln Arg Glu Ala Leu
        35                  40                  45

Phe Asn Ala Ile Ala Ala Tyr
    50                  55

<210> SEQ ID NO 9
<211> LENGTH: 55
<212> TYPE: PRT
<213> ORGANISM: Salmonella typhimurium

<400> SEQUENCE: 9

Val Lys Ala Thr Ile Pro Leu Leu Val Glu Thr Gly Pro Lys Leu Thr
 1               5                  10                  15

Ala His Phe Tyr Asp Arg Met Phe Thr His Asn Pro Glu Leu Lys Glu
            20                  25                  30

Ile Phe Asn Met Ser Asn Gln Arg Asn Gly Asp Gln Arg Glu Ala Leu
        35                  40                  45

Phe Asn Ala Ile Ala Ala Tyr
    50                  55

<210> SEQ ID NO 10
<211> LENGTH: 56
<212> TYPE: PRT
<213> ORGANISM: Ralstonia eutropha

<400> SEQUENCE: 10

Ile Val Lys Ala Thr Ala Pro Val Leu Ala Glu His Gly Tyr Asp Ile
 1               5                  10                  15

Ile Lys Cys Phe Tyr Gln Arg Met Phe Glu Ala His Pro Glu Leu Lys
            20                  25                  30

Asn Val Phe Asn Met Ala His Gln Glu Gln Gly Gln Gln Gln Gln Ala
        35                  40                  45

Leu Ala Arg Ala Val Tyr Ala Tyr
    50                  55
```

-continued

<210> SEQ ID NO 11
<211> LENGTH: 56
<212> TYPE: PRT
<213> ORGANISM: Vibrio parahaemolyticus

<400> SEQUENCE: 11

Ile Val Lys Ala Thr Ala Pro Leu Ile Ala Glu Thr Gly Pro Lys Leu
1 5 10 15

Thr Ala His Phe Tyr Asp Arg Met Phe Thr His Asn Pro Glu Leu Lys
20 25 30

Asp Ile Phe Asn Met Ser Asn Gln Arg Asn Gly Asp Gln Arg Glu Ala
35 40 45

Leu Phe Asn Ala Ile Cys Ala Tyr
50 55

<210> SEQ ID NO 12
<211> LENGTH: 56
<212> TYPE: PRT
<213> ORGANISM: Clostridium perfringens

<400> SEQUENCE: 12

Ile Ile Lys Ser Thr Val Pro Val Leu Lys Ser Asn Gly Leu Glu Ile
1 5 10 15

Thr Lys Thr Phe Tyr Lys Asn Met Phe Glu Gln Asn Pro Glu Val Lys
20 25 30

Pro Leu Phe Asn Met Asn Lys Gln Glu Ser Glu Glu Gln Pro Lys Ala
35 40 45

Leu Ala Met Ala Ile Leu Ala Val
50 55

<210> SEQ ID NO 13
<211> LENGTH: 56
<212> TYPE: PRT
<213> ORGANISM: Fusarium oxysporum

<400> SEQUENCE: 13

Ile Val Lys Ser Thr Ala Pro Ile Leu Lys Glu His Gly Lys Thr Ile
1 5 10 15

Thr Thr Thr Phe Tyr Arg Asn Met Leu Gly Ala His Pro Glu Leu Lys
20 25 30

Asn Tyr Phe Ser Leu Arg Asn Gln Gln Thr Gly Ala Gln Gln Ala Ala
35 40 45

Leu Ala Asn Ser Val Leu Ala Tyr
50 55

<210> SEQ ID NO 14
<211> LENGTH: 53
<212> TYPE: PRT
<213> ORGANISM: Aquifex aeolicus

<400> SEQUENCE: 14

Val Ile Lys Ser Thr Val Pro Leu Leu Lys Glu His Gly Thr Glu Ile
1 5 10 15

Thr Ala Arg Met Tyr Glu Leu Leu Phe Ser Lys Tyr Pro Lys Thr Lys
20 25 30

Glu Leu Phe Ala Gly Ala Ser Glu Glu Gln Pro Lys Lys Leu Ala Asn
35 40 45

Ala Ile Ile Ala Tyr
50

```
<210> SEQ ID NO 15
<211> LENGTH: 56
<212> TYPE: PRT
<213> ORGANISM: Bacillus subtilis

<400> SEQUENCE: 15

Ile Ile Lys Ser Thr Val Pro Val Leu Gln Gln His Gly Glu Thr Ile
 1               5                  10                  15

Thr Gly Arg Phe Tyr Asp Arg Met Phe Gln Asp His Pro Glu Leu Leu
            20                  25                  30

Asn Ile Phe Asn Gln Thr Asn Gln Lys Lys Thr Gln Arg Thr Ala
        35                  40                  45

Leu Ala Asn Ala Val Ile Ala Ala
    50                  55

<210> SEQ ID NO 16
<211> LENGTH: 56
<212> TYPE: PRT
<213> ORGANISM: Xenopus laevis

<400> SEQUENCE: 16

Ile Lys Ala Ile Met Pro Ser Ile Ala Ala His Gly Asp Thr Phe Gly
 1               5                  10                  15

Gly Glu Ala Leu Tyr Arg Met Phe Leu Val Asn Pro Lys Thr Lys Thr
            20                  25                  30

Tyr Phe Pro Ser Phe Asp Phe His His Asn Ser Lys Gln Ile Thr Ser
        35                  40                  45

His Gly Lys Lys Val Val Asp Ala
    50                  55

<210> SEQ ID NO 17
<211> LENGTH: 57
<212> TYPE: PRT
<213> ORGANISM: Chironomus thummi

<400> SEQUENCE: 17

Asp Gln Leu Ala Leu Phe Lys Ser Ser Trp Asn Thr Val Lys His Asn
 1               5                  10                  15

Glu Val Asp Ile Leu Tyr Ala Val Phe Lys Ala Asn Pro Asp Ile Gln
            20                  25                  30

Ala Lys Phe Pro Gln Phe Ala Gly Lys Asp Leu Asp Ser Ile Lys Asp
        35                  40                  45

Ser Ala Asp Phe Ala Val His Ser Gly
    50                  55

<210> SEQ ID NO 18
<211> LENGTH: 56
<212> TYPE: PRT
<213> ORGANISM: Xenopus borealis

<400> SEQUENCE: 18

Ile Lys Ala Ile Met Pro Ser Ile Ala Ala His Gly Asp Lys Phe Gly
 1               5                  10                  15

Gly Glu Ala Leu Tyr Arg Met Phe Leu Val Asn Pro Lys Thr Lys Thr
            20                  25                  30

Tyr Phe Pro Thr Phe Asp Phe His His Asn Ser Lys Gln Ile Ser Ala
        35                  40                  45

His Gly Lys Lys Val Val Asp Ala
    50                  55
```

<210> SEQ ID NO 19
<211> LENGTH: 56
<212> TYPE: PRT
<213> ORGANISM: Xenopus borealis

<400> SEQUENCE: 19

Ile Lys Ala Ile Leu Pro Ser Ile Ala Ala His Gly Asp Lys Phe Gly
 1               5                  10                  15

Gly Glu Ala Leu Tyr Arg Met Phe Leu Ile Asn Pro Lys Thr Lys Thr
            20                  25                  30

Tyr Phe Pro Asn Phe Asp Phe His His Asn Ser Lys Gln Ile Ser Ala
        35                  40                  45

His Gly Lys Lys Val Val Asp Ala
    50                  55

<210> SEQ ID NO 20
<211> LENGTH: 57
<212> TYPE: PRT
<213> ORGANISM: Chironomus thummi

<400> SEQUENCE: 20

Gln Ala Ile Leu Ile Arg Ser Ser Trp Glu Asp Glu Val Lys His Asn
 1               5                  10                  15

Glu Val Asp Ile Leu Tyr Ala Ile Phe Lys Ala Asn Pro Asp Ile Gln
            20                  25                  30

Ala Arg Phe Pro Gln Phe Ala Gly Lys Asp Leu Asp Ser Ile Lys Thr
        35                  40                  45

Thr Gly Gln Phe Ala Val His Ala Gly
    50                  55

<210> SEQ ID NO 21
<211> LENGTH: 55
<212> TYPE: PRT
<213> ORGANISM: Pichia norvegensis

<400> SEQUENCE: 21

Leu Gln Ser Leu Ala Pro Val Val Lys Glu His Gly Val Thr Val Thr
 1               5                  10                  15

Ser Thr Met Tyr Lys Tyr Met Phe Gln Thr Tyr Pro Glu Val Arg Ser
            20                  25                  30

Tyr Phe Asn Met Thr Asn Gln Lys Thr Gly Arg Gln Pro Lys Val Leu
        35                  40                  45

Ala Phe Ser Leu Tyr Gln Tyr
    50                  55

<210> SEQ ID NO 22
<211> LENGTH: 56
<212> TYPE: PRT
<213> ORGANISM: Saccharomyces cerevisiae

<400> SEQUENCE: 22

Ile Ile Lys Ala Thr Val Pro Val Leu Glu Gln Gln Gly Thr Val Ile
 1               5                  10                  15

Thr Arg Thr Phe Tyr Lys Asn Met Leu Thr Glu His Thr Glu Leu Leu
            20                  25                  30

Asn Ile Phe Asn Arg Thr Asn Gln Lys Val Gly Ala Gln Pro Asn Ala
        35                  40                  45

Leu Ala Thr Thr Val Leu Ala Ala
    50                  55

<210> SEQ ID NO 23
<211> LENGTH: 41
<212> TYPE: PRT
<213> ORGANISM: Physeter catodon

<400> SEQUENCE: 23

Gly Gln Asp Ile Leu Ile Arg Leu Phe Lys Ser His Pro Glu Thr Leu
 1               5                  10                  15

Glu Lys Phe Asp Arg Phe Lys His Leu Lys Thr Glu Ala Glu Met Lys
            20                  25                  30

Ala Ser Glu Asp Leu Lys Lys His Gly
        35                  40

<210> SEQ ID NO 24
<211> LENGTH: 41
<212> TYPE: PRT
<213> ORGANISM: Kogia simus

<400> SEQUENCE: 24

Gly Gln Asp Ile Leu Ile Arg Leu Phe Lys His His Pro Glu Thr Leu
 1               5                  10                  15

Glu Lys Phe Asp Arg Phe Lys His Leu Lys Ser Glu Ala Glu Met Lys
            20                  25                  30

Ala Ser Glu Asp Leu Lys Lys His Gly
        35                  40

<210> SEQ ID NO 25
<211> LENGTH: 41
<212> TYPE: PRT
<213> ORGANISM: Rousettus aegyptiacus

<400> SEQUENCE: 25

Gly Gln Glu Val Leu Ile Arg Leu Phe Lys Gly His Pro Glu Thr Leu
 1               5                  10                  15

Glu Lys Phe Asp Lys Phe Lys His Leu Lys Ser Glu Asp Glu Met Lys
            20                  25                  30

Ala Ser Glu Asp Leu Lys Lys His Gly
        35                  40

<210> SEQ ID NO 26
<211> LENGTH: 41
<212> TYPE: PRT
<213> ORGANISM: Delphinus delphis

<400> SEQUENCE: 26

Gly Gln Asp Val Leu Ile Arg Leu Phe Lys Gly His Pro Glu Thr Leu
 1               5                  10                  15

Glu Lys Phe Asp Lys Phe Lys His Leu Lys Thr Glu Ala Asp Met Lys
            20                  25                  30

Ala Ser Glu Asp Leu Lys Lys His Gly
        35                  40

<210> SEQ ID NO 27
<211> LENGTH: 41
<212> TYPE: PRT
<213> ORGANISM: Globicephala melas

```
<400> SEQUENCE: 27

Gly Gln Asp Ile Leu Ile Arg Leu Phe Lys Gly His Pro Glu Thr Leu
 1               5                  10                 15

Glu Lys Phe Asp Lys Phe Lys His Leu Lys Thr Glu Ala Asp Met Lys
                20                  25                 30

Ala Ser Glu Asp Leu Lys Lys His Gly
            35                  40

<210> SEQ ID NO 28
<211> LENGTH: 41
<212> TYPE: PRT
<213> ORGANISM: Aethia pygmaea

<400> SEQUENCE: 28

Gly His Gln Val Leu Met Arg Leu Phe Gln Asp His Pro Glu Thr Leu
 1               5                  10                 15

Asp Arg Phe Asp Lys Phe Lys Gly Leu Lys Thr Pro Asp Gln Met Lys
                20                  25                 30

Gly Ser Glu Asp Leu Lys Lys His Gly
            35                  40

<210> SEQ ID NO 29
<211> LENGTH: 39
<212> TYPE: PRT
<213> ORGANISM: Mustelus antarcticus

<400> SEQUENCE: 29

Gly Gln Asn Ile Leu Leu Arg Leu Phe Glu Gln Tyr Pro Glu Ser Gln
 1               5                  10                 15

Asn His Phe Pro Lys Phe Lys Asn Lys Ser Leu Gly Glu Leu Lys Asp
                20                  25                 30

Thr Ala Asp Ile Lys Ala Gln
            35

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence:  Template
      sequence
<221> NAME/KEY: UNSURE
<222> LOCATION: (1)..(18)
<223> OTHER INFORMATION: Xaa at positions 1-18, 22, and 30 is unknown

<400> SEQUENCE: 30

Xaa Xaa Xaa Xaa Xaa Xaa Xaa Xaa Xaa Xaa Xaa Xaa Xaa Xaa Xaa Xaa
 1               5                  10                 15

Xaa Xaa Ala Gln Arg Xaa Arg Leu Ala Gln Ile His Ala Xaa Lys Gly
                20                  25                 30

Lys Ile Pro Asp Trp Tyr Leu
            35

<210> SEQ ID NO 31
<211> LENGTH: 39
<212> TYPE: PRT
<213> ORGANISM: Physeter catodon
```

```
<400> SEQUENCE: 31

Val Thr Val Leu Thr Ala Leu Gly Ala Ile Leu Lys Lys Lys Gly His
  1               5                  10                  15

His Glu Ala Glu Leu Lys Pro Leu Ala Gln Ser His Ala Thr Lys His
             20                  25                  30

Lys Ile Pro Ile Lys Tyr Leu
         35

<210> SEQ ID NO 32
<211> LENGTH: 39
<212> TYPE: PRT
<213> ORGANISM: Kogia simus

<400> SEQUENCE: 32

Val Thr Val Leu Thr Ala Leu Gly Ala Ile Leu Lys Lys Lys Gly His
  1               5                  10                  15

His Glu Ala Glu Leu Lys Pro Leu Ala Gln Ser His Ala Thr Lys His
             20                  25                  30

Lys Ile Pro Ile Lys Tyr Leu
         35

<210> SEQ ID NO 33
<211> LENGTH: 39
<212> TYPE: PRT
<213> ORGANISM: Rousettus aegyptiacus

<400> SEQUENCE: 33

Ala Thr Val Leu Thr Ala Leu Gly Gly Ile Leu Lys Lys Lys Gly Gln
  1               5                  10                  15

His Glu Ala Gln Leu Lys Pro Leu Ala Gln Ser His Ala Thr Lys His
             20                  25                  30

Lys Ile Pro Val Lys Tyr Leu
         35

<210> SEQ ID NO 34
<211> LENGTH: 39
<212> TYPE: PRT
<213> ORGANISM: Delphinus delphis

<400> SEQUENCE: 34

Asn Thr Val Leu Thr Ala Leu Gly Ala Ile Leu Lys Lys Lys Gly His
  1               5                  10                  15

His Asp Ala Glu Leu Lys Pro Leu Ala Gln Ser His Ala Thr Lys His
             20                  25                  30

Lys Ile Pro Ile Lys Tyr Leu
         35

<210> SEQ ID NO 35
<211> LENGTH: 39
<212> TYPE: PRT
<213> ORGANISM: Globicephala melas

<400> SEQUENCE: 35

Asn Thr Val Leu Thr Ala Leu Gly Ala Ile Leu Lys Lys Lys Gly His
  1               5                  10                  15

His Glu Ala Glu Leu Lys Pro Leu Ala Gln Ser His Ala Thr Lys His
             20                  25                  30

Lys Ile Pro Ile Lys Tyr Leu
         35
```

<210> SEQ ID NO 36
<211> LENGTH: 39
<212> TYPE: PRT
<213> ORGANISM: Aethia pygmaea

<400> SEQUENCE: 36

Val Thr Val Leu Thr Gln Leu Gly Lys Ile Leu Lys Gln Lys Gly Asn
 1               5                  10                  15

His Glu Ser Glu Leu Lys Pro Leu Ala Gln Thr His Ala Thr Lys His
            20                  25                  30

Lys Ile Pro Val Lys Tyr Leu
        35

<210> SEQ ID NO 37
<211> LENGTH: 39
<212> TYPE: PRT
<213> ORGANISM: Bacillus subtilis

<400> SEQUENCE: 37

Leu Lys Arg His Ile Gln Glu Met Phe Ala Gly Val Ile Asp Asp Glu
 1               5                  10                  15

Phe Ile Glu Lys Arg Asn Arg Ile Ala Ser Ile His Leu Arg Ile Gly
            20                  25                  30

Leu Leu Pro Lys Trp Tyr Met
        35

<210> SEQ ID NO 38
<211> LENGTH: 40
<212> TYPE: PRT
<213> ORGANISM: Mustelus antarcticus

<400> SEQUENCE: 38

Ala Asp Thr Val Leu Ser Ala Leu Gly Asn Ile Val Lys Lys Lys Gly
 1               5                  10                  15

Ser His Ser Gln Pro Val Lys Ala Leu Ala Ala Thr His Ile Thr Thr
            20                  25                  30

His Lys Ile Pro Pro His Tyr Phe
        35                  40

<210> SEQ ID NO 39
<211> LENGTH: 39
<212> TYPE: PRT
<213> ORGANISM: Halobacterium salinarum

<400> SEQUENCE: 39

Gln Ala Glu Tyr Leu Leu Gly Leu Gly Arg Gly Glu Tyr Asp Thr Glu
 1               5                  10                  15

Tyr Ala Ala Gln Arg Ala Arg Ile Gly Lys Ile His Asp Val Leu Gly
            20                  25                  30

Leu Gly Pro Asp Val Tyr Leu
        35

<210> SEQ ID NO 40
<211> LENGTH: 29
<212> TYPE: DNA
<213> ORGANISM: Artificial Sequence
<220> FEATURE:
<223> OTHER INFORMATION: Description of Artificial Sequence: Cloning
      primer

<400> SEQUENCE: 40
ccgaattcca tatgagcaac gataatgac                                    29

```
<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Cloning
      primer
<221> NAME/KEY: unsure
<222> LOCATION: (13)..(14)
<223> OTHER INFORMATION: n at positions 13 and 14 is unknown

<400> SEQUENCE: 41
cctctagagg atnnctagct gagcttgccg acc                                    33

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Cloning
      primer
<221> NAME/KEY: unsure
<222> LOCATION: (29)
<223> OTHER INFORMATION: n at position 29 is unknown

<400> SEQUENCE: 42
tatgggatcc cttgttcatc acgggtctnt tgg                                    33

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Cloning
      primer

<400> SEQUENCE: 43
gataaagctt gatcatagct cagttgaccg                                        30

<210> SEQ ID NO 44
<211> LENGTH: 32
<212> TYPE: DNA
<213> ORGANISM: Artificial Sequence
<220> FEATURE:
<223> OTHER INFORMATION: Description of Artificial Sequence: Cloning
      primer

<400> SEQUENCE: 44
tgctgaattc gcagctttca ttcatgtttc cc                                     32

<210> SEQ ID NO 45
<211> LENGTH: 36
<212> TYPE: DNA
<213> ORGANISM: Artificial Sequence
<220> FEATURE:
<223> OTHER INFORMATION: Description of Artificial Sequence: Cloning
      primer

<400> SEQUENCE: 45
ttagggatcc gtcaactgat ttttaattta agttac                                 36

<210> SEQ ID NO 46
<211> LENGTH: 42
<212> TYPE: DNA
<213> ORGANISM: Artificial Sequence
<220> FEATURE:
<223> OTHER INFORMATION: Description of Artificial Sequence: Cloning
      primer
```

```
<400> SEQUENCE: 46
atatggatcc aagggggatc attgtaatgt tatttaaaaa ag                          42

<210> SEQ ID NO 47
<211> LENGTH: 46
<212> TYPE: DNA
<213> ORGANISM: Artificial Sequence
<220> FEATURE:
<223> OTHER INFORMATION: Description of Artificial Sequence: Cloning
      primer

<400> SEQUENCE: 47
attactgcag caactgattt ttaatttaag tttacataat gaacgc                      46

<210> SEQ ID NO 48
<211> LENGTH: 29
<212> TYPE: DNA
<213> ORGANISM: Artificial Sequence
<220> FEATURE:
<223> OTHER INFORMATION: Description of Artificial Sequence: Cloning
      primer

<400> SEQUENCE: 48
ccgaattcca tatgagcaac gataatgac                                         29

<210> SEQ ID NO 49
<211> LENGTH: 35
<212> TYPE: DNA
<213> ORGANISM: Artificial Sequence
<220> FEATURE:
<223> OTHER INFORMATION: Description of Artificial Sequence: Cloning
      primer

<400> SEQUENCE: 49
ctctagagga tccctagtcg tcggcaagcg cgtcc                                  35

<210> SEQ ID NO 50
<211> LENGTH: 35
<212> TYPE: DNA
<213> ORGANISM: Artificial Sequence
<220> FEATURE:
<223> OTHER INFORMATION: Description of Artificial Sequence: Cloning
      primer
<221> NAME/KEY: unsure
<222> LOCATION: (15)
<223> OTHER INFORMATION: n at position 15  is unknown

<400> SEQUENCE: 50
cctctagagg atccntagac gtcagccatg cggtc                                  35

<210> SEQ ID NO 51
<211> LENGTH: 39
<212> TYPE: DNA
<213> ORGANISM: Artificial Sequence
<220> FEATURE:
<223> OTHER INFORMATION: Description of Artificial Sequence: Cloning
      primer

<400> SEQUENCE: 51
cctctagagg atccctaggc gacgtcctgc gaggtcgcc                              39

<210> SEQ ID NO 52
<211> LENGTH: 40
<212> TYPE: DNA
<213> ORGANISM: Artificial Sequence
```

```
<220> FEATURE:
<223> OTHER INFORMATION: Description of Artificial Sequence: Cloning
      primer

<400> SEQUENCE: 52
cctctagagg atccctacgc gttcgccaac tcctggcggc                           40

<210> SEQ ID NO 53
<211> LENGTH: 39
<212> TYPE: DNA
<213> ORGANISM: Artificial Sequence
<220> FEATURE:
<223> OTHER INFORMATION: Description of Artificial Sequence: Cloning
      primer

<400> SEQUENCE: 53
cctctagagg atccctagat gtaggtgtcc attgcgatc                            39

<210> SEQ ID NO 54
<211> LENGTH: 38
<212> TYPE: DNA
<213> ORGANISM: Artificial Sequence
<220> FEATURE:
<223> OTHER INFORMATION: Description of Artificial Sequence: Cloning
      primer

<400> SEQUENCE: 54
cctctagagg atccctaccg ggccacgagt tcgtcgac                             38

<210> SEQ ID NO 55
<211> LENGTH: 38
<212> TYPE: DNA
<213> ORGANISM: Artificial Sequence
<220> FEATURE:
<223> OTHER INFORMATION: Description of Artificial Sequence: Cloning
      primer

<400> SEQUENCE: 55
cctctagagg atccctactg gcggctgtcg atctcgtc                             38

<210> SEQ ID NO 56
<211> LENGTH: 38
<212> TYPE: DNA
<213> ORGANISM: Artificial Sequence
<220> FEATURE:
<223> OTHER INFORMATION: Description of Artificial Sequence: Cloning
      primer

<400> SEQUENCE: 56
cctctagagg atccctactc gtcgtggagg cgctgggc                             38

<210> SEQ ID NO 57
<211> LENGTH: 39
<212> TYPE: DNA
<213> ORGANISM: Artificial Sequence
<220> FEATURE:
<223> OTHER INFORMATION: Description of Artificial Sequence: Cloning
      primer

<400> SEQUENCE: 57
cctctagagg atccctactg ggcgtacgag tcgatgtag                            39

<210> SEQ ID NO 58
<211> LENGTH: 42
<212> TYPE: DNA
<213> ORGANISM: Artificial Sequence
```

-continued

```
<220> FEATURE:
<223> OTHER INFORMATION: Description of Artificial Sequence:  Cloning
      primer

<400> SEQUENCE: 58
cctctagagg atccctaggc gtacgagtcg atgtaggtgt cc                          42

<210> SEQ ID NO 59
<211> LENGTH: 39
<212> TYPE: DNA
<213> ORGANISM: Artificial Sequence
<220> FEATURE:
<223> OTHER INFORMATION: Description of Artificial Sequence:  Cloning
      primer

<400> SEQUENCE: 59
cctctagagg atccctagta cgagtcgatg taggtgtcc                              39

<210> SEQ ID NO 60
<211> LENGTH: 42
<212> TYPE: DNA
<213> ORGANISM: Artificial Sequence
<220> FEATURE:
<223> OTHER INFORMATION: Description of Artificial Sequence:  Cloning
      primer

<400> SEQUENCE: 60
cctctagagg atccctacga gtcgatgtag gtgtccattg cg                          42

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence:  Cloning
      primer

<400> SEQUENCE: 61
cctctagagg atccctagtc gatgtaggtg tccattgcg                              39

<210> SEQ ID NO 62
<211> LENGTH: 29
<212> TYPE: DNA
<213> ORGANISM: Artificial Sequence
<220> FEATURE:
<223> OTHER INFORMATION: Description of Artificial Sequence:  Cloning
      primer

<400> SEQUENCE: 62
ccgaattcca tatgagcaac gataatgac                                         29

<210> SEQ ID NO 63
<211> LENGTH: 27
<212> TYPE: DNA
<213> ORGANISM: Artificial Sequence
<220> FEATURE:
<223> OTHER INFORMATION: Description of Artificial Sequence:  Cloning
      primer

<400> SEQUENCE: 63
cctctagact agctgagctt gccgacc                                           27

<210> SEQ ID NO 64
<211> LENGTH: 35
<212> TYPE: DNA
<213> ORGANISM: Artificial Sequence
```

```
<220> FEATURE:
<223> OTHER INFORMATION: Description of Artificial Sequence: Cloning
      primer

<400> SEQUENCE: 64
ggaacgggat cgacggggcc gcactcgcgg accgg                                    35

<210> SEQ ID NO 65
<211> LENGTH: 35
<212> TYPE: DNA
<213> ORGANISM: Artificial Sequence
<220> FEATURE:
<223> OTHER INFORMATION: Description of Artificial Sequence: Cloning
      primer

<400> SEQUENCE: 65
ccggtccgcg agtgcggccc cgtcgatccc gttcc                                    35

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: Cloning
      primer

<400> SEQUENCE: 66
gaccgacttc tacgacgcct tggagtccta cgagcg                                   36

<210> SEQ ID NO 67
<211> LENGTH: 36
<212> TYPE: DNA
<213> ORGANISM: Artificial Sequence
<220> FEATURE:
<223> OTHER INFORMATION: Description of Artificial Sequence: Cloning
      primer

<400> SEQUENCE: 67
cgctcgtagg actccaaggc gtcgtagaag tcggtc                                   36

<210> SEQ ID NO 68
<211> LENGTH: 35
<212> TYPE: DNA
<213> ORGANISM: Artificial Sequence
<220> FEATURE:
<223> OTHER INFORMATION: Description of Artificial Sequence: Cloning
      primer

<400> SEQUENCE: 68
ccgtatcggg aagatagccg acgtgctcgg gctcg                                    35

<210> SEQ ID NO 69
<211> LENGTH: 35
<212> TYPE: DNA
<213> ORGANISM: Artificial Sequence
<220> FEATURE:
<223> OTHER INFORMATION: Description of Artificial Sequence: Cloning
      primer

<400> SEQUENCE: 69
cgagcccgag cacgtcggct atcttcccga tacgg                                    35

<210> SEQ ID NO 70
<211> LENGTH: 36
<212> TYPE: DNA
<213> ORGANISM: Artificial Sequence
```

```
<220> FEATURE:
<223> OTHER INFORMATION: Description of Artificial Sequence:  Cloning
      primer

<400> SEQUENCE: 70
cgtacgccca gcgcctcgcc gacgagatcg acagcc                                   36

<210> SEQ ID NO 71
<211> LENGTH: 36
<212> TYPE: DNA
<213> ORGANISM: Artificial Sequence
<220> FEATURE:
<223> OTHER INFORMATION: Description of Artificial Sequence:  Cloning
      primer

<400> SEQUENCE: 71
ggctgtcgat ctcgtcggcg aggcgctggg cgtacg                                   36

<210> SEQ ID NO 72
<211> LENGTH: 36
<212> TYPE: DNA
<213> ORGANISM: Artificial Sequence
<220> FEATURE:
<223> OTHER INFORMATION: Description of Artificial Sequence:  Cloning
      primer

<400> SEQUENCE: 72
gcgaacgcgg tcgccacggc cgtggaagca ccgctg                                   36

<210> SEQ ID NO 73
<211> LENGTH: 37
<212> TYPE: DNA
<213> ORGANISM: Artificial Sequence
<220> FEATURE:
<223> OTHER INFORMATION: Description of Artificial Sequence:  Cloning
      primer
<221> NAME/KEY: unsure
<222> LOCATION: (23)
<223> OTHER INFORMATION: Y at position 23 in this sequence is either t
      or c

<400> SEQUENCE: 73
cagcggtgct tccacggccg tcygcgaccg cgttcgc                                  37

<210> SEQ ID NO 74
<211> LENGTH: 42
<212> TYPE: DNA
<213> ORGANISM: Artificial Sequence
<220> FEATURE:
<223> OTHER INFORMATION: Description of Artificial Sequence:  Cloning
      primer

<400> SEQUENCE: 74
atatggatcc aaggggatc attgtaatgt tatttaaaaa ag                             42

<210> SEQ ID NO 75
<211> LENGTH: 46
<212> TYPE: DNA
<213> ORGANISM: Artificial Sequence
<220> FEATURE:
<223> OTHER INFORMATION: Description of Artificial Sequence:  Cloning
      primer

<400> SEQUENCE: 75
attactgcag caactgattt ttaatttaag tttacataat gaacgc                        46
```

```
<210> SEQ ID NO 76
<211> LENGTH: 153
<212> TYPE: PRT
<213> ORGANISM: Sperm-whale myoglobin

<400> SEQUENCE: 76
```

| Val | Leu | Ser | Glu | Gly | Glu | Trp | Gln | Leu | Val | Leu | His | Val | Trp | Ala | Lys |
|---|---|---|---|---|---|---|---|---|---|---|---|---|---|---|---|
| 1 | | | | 5 | | | | | 10 | | | | | 15 | |

| Val | Glu | Ala | Asp | Val | Ala | Gly | His | Gly | Gln | Asp | Ile | Leu | Ile | Arg | Leu |
|---|---|---|---|---|---|---|---|---|---|---|---|---|---|---|---|
| | | | 20 | | | | | 25 | | | | | 30 | | |

| Phe | Lys | Ser | His | Pro | Glu | Thr | Leu | Glu | Lys | Phe | Asp | Arg | Phe | Lys | His |
|---|---|---|---|---|---|---|---|---|---|---|---|---|---|---|---|
| | | 35 | | | | | 40 | | | | | 45 | | | |

| Leu | Lys | Thr | Glu | Ala | Glu | Met | Lys | Ala | Ser | Glu | Asp | Leu | Lys | Lys | His |
|---|---|---|---|---|---|---|---|---|---|---|---|---|---|---|---|
| | 50 | | | | | 55 | | | | | 60 | | | | |

| Gly | Val | Thr | Val | Leu | Thr | Ala | Leu | Gly | Ala | Ile | Leu | Lys | Lys | Lys | Gly |
|---|---|---|---|---|---|---|---|---|---|---|---|---|---|---|---|
| 65 | | | | | 70 | | | | | 75 | | | | | 80 |

| His | His | Glu | Ala | Glu | Leu | Lys | Pro | Leu | Ala | Gln | Ser | His | Ala | Thr | Lys |
|---|---|---|---|---|---|---|---|---|---|---|---|---|---|---|---|
| | | | | 85 | | | | | 90 | | | | | 95 | |

| His | Lys | Ile | Pro | Ile | Lys | Tyr | Leu | Glu | Phe | Ile | Ser | Glu | Ala | Ile | Ile |
|---|---|---|---|---|---|---|---|---|---|---|---|---|---|---|---|
| | | | | 100 | | | | | 105 | | | | | 110 | |

| His | Val | Leu | His | Ser | Arg | His | Pro | Gly | Asp | Phe | Gly | Ala | Asp | Ala | Gln |
|---|---|---|---|---|---|---|---|---|---|---|---|---|---|---|---|
| | | | 115 | | | | | 120 | | | | | 125 | | |

| Gly | Ala | Met | Asn | Lys | Ala | Leu | Glu | Leu | Phe | Arg | Lys | Asp | Ile | Ala | Ala |
|---|---|---|---|---|---|---|---|---|---|---|---|---|---|---|---|
| | 130 | | | | | 135 | | | | | 140 | | | | |

| Lys | Tyr | Lys | Glu | Leu | Gly | Tyr | Gln | Gly |
|---|---|---|---|---|---|---|---|---|
| 145 | | | | | 150 | | | |

```
<210> SEQ ID NO 77
<211> LENGTH: 184
<212> TYPE: PRT
<213> ORGANISM: Halobacterium salinarum

<400> SEQUENCE: 77
```

| Met | Ser | Asn | Asp | Asn | Asp | Thr | Leu | Val | Thr | Ala | Asp | Val | Arg | Asn | Gly |
|---|---|---|---|---|---|---|---|---|---|---|---|---|---|---|---|
| 1 | | | | 5 | | | | | 10 | | | | | 15 | |

| Ile | Asp | Gly | His | Ala | Leu | Ala | Asp | Arg | Ile | Gly | Leu | Asp | Glu | Ala | Glu |
|---|---|---|---|---|---|---|---|---|---|---|---|---|---|---|---|
| | | | 20 | | | | | 25 | | | | | 30 | | |

| Ile | Ala | Trp | Arg | Leu | Ser | Phe | Thr | Gly | Ile | Asp | Asp | Thr | Met | Ala |
|---|---|---|---|---|---|---|---|---|---|---|---|---|---|---|
| | | 35 | | | | | 40 | | | | | 45 | | |

| Ala | Leu | Ala | Ala | Glu | Gln | Pro | Leu | Phe | Glu | Ala | Thr | Ala | Asp | Ala | Leu |
|---|---|---|---|---|---|---|---|---|---|---|---|---|---|---|---|
| | 50 | | | | | 55 | | | | | 60 | | | | |

| Val | Thr | Asp | Phe | Tyr | Asp | His | Leu | Glu | Ser | Tyr | Glu | Arg | Thr | Gln | Asp |
|---|---|---|---|---|---|---|---|---|---|---|---|---|---|---|---|
| 65 | | | | | 70 | | | | | 75 | | | | | 80 |

| Leu | Phe | Ala | Asn | Ser | Thr | Lys | Thr | Val | Glu | Gln | Leu | Lys | Glu | Thr | Gln |
|---|---|---|---|---|---|---|---|---|---|---|---|---|---|---|---|
| | | | | 85 | | | | | 90 | | | | | 95 | |

| Ala | Glu | Tyr | Leu | Leu | Gly | Leu | Gly | Arg | Gly | Glu | Tyr | Asp | Thr | Glu | Tyr |
|---|---|---|---|---|---|---|---|---|---|---|---|---|---|---|---|
| | | | | 100 | | | | | 105 | | | | | 110 | |

| Ala | Ala | Gln | Arg | Ala | Arg | Ile | Gly | Lys | Ile | His | Asp | Val | Leu | Gly | Leu |
|---|---|---|---|---|---|---|---|---|---|---|---|---|---|---|---|
| | | | 115 | | | | | 120 | | | | | 125 | | |

| Gly | Pro | Asp | Val | Tyr | Leu | Gly | Ala | Tyr | Thr | Arg | Tyr | Thr | Gly | Leu |
|---|---|---|---|---|---|---|---|---|---|---|---|---|---|---|
| | 130 | | | | | 135 | | | | | 140 | | | |

| Leu | Asp | Ala | Leu | Ala | Asp | Asp | Val | Val | Ala | Asp | Arg | Gly | Glu | Glu | Ala |
|---|---|---|---|---|---|---|---|---|---|---|---|---|---|---|---|
| 145 | | | | | 150 | | | | | 155 | | | | | 160 |

-continued

```
Ala Ala Ala Val Asp Glu Leu Val Ala Arg Phe Leu Pro Met Leu Lys
                165                 170                 175

Leu Leu Thr Phe Asp Gln Gln Ile
            180

<210> SEQ ID NO 78
<211> LENGTH: 175
<212> TYPE: PRT
<213> ORGANISM: Bacillus subtilis

<400> SEQUENCE: 78

Leu Leu Phe Lys Lys Asp Arg Lys Gln Glu Thr Ala Tyr Phe Ser Asp
  1               5                  10                  15

Ser Asn Gly Gln Gln Lys Asn Arg Ile Gln Leu Thr Asn Lys His Ala
             20                  25                  30

Asp Val Lys Lys Gln Leu Lys Met Val Arg Leu Gly Asp Ala Glu Leu
         35                  40                  45

Tyr Val Leu Glu Gln Leu Gln Pro Leu Ile Gln Glu Asn Ile Val Asn
     50                  55                  60

Ile Val Asp Ala Phe Tyr Lys Asn Leu Asp His Glu Ser Ser Leu Met
 65                  70                  75                  80

Asp Ile Ile Asn Asp His Ser Ser Val Asp Arg Leu Lys Gln Thr Leu
                 85                  90                  95

Lys Arg His Ile Gln Glu Met Phe Ala Gly Val Ile Asp Asp Glu Phe
            100                 105                 110

Ile Glu Lys Arg Asn Arg Ile Ala Ser Ile His Leu Arg Ile Gly Leu
        115                 120                 125

Leu Pro Lys Trp Tyr Met Gly Ala Phe Gln Glu Leu Leu Leu Ser Met
    130                 135                 140

Ile Asp Ile Tyr Glu Ala Ser Ile Thr Asn Gln Gln Glu Leu Leu Lys
145                 150                 155                 160

Ala Ile Lys Ala Thr Thr Lys Ile Leu Asn Leu Glu Gln Gln Leu
                165                 170                 175

<210> SEQ ID NO 79
<211> LENGTH: 274
<212> TYPE: PRT
<213> ORGANISM: Escherichia coli

<400> SEQUENCE: 79

Leu Met Arg Thr Val Gly Asp Val Arg Asn Gly Ala Asn Ala Ile Tyr
  1               5                  10                  15

Ser Gly Ala Ser Glu Ile Ala Thr Gly Asn Asn Asp Leu Ser Ser Arg
             20                  25                  30

Thr Glu Gln Gln Ala Ala Ser Leu Glu Glu Thr Ala Ala Ser Met Glu
         35                  40                  45

Gln Leu Thr Ala Thr Val Lys Gln Asn Ala Glu Asn Ala Arg Gln Ala
     50                  55                  60

Ser His Leu Ala Leu Ser Ala Ser Glu Thr Ala Gln Arg Gly Gly Lys
 65                  70                  75                  80

Val Val Asp Asn Val Val Gln Thr Met Arg Asp Ile Ser Thr Ser Ser
                 85                  90                  95

Gln Lys Ile Ala Asp Ile Ile Ser Val Ile Asp Gly Ile Ala Phe Gln
            100                 105                 110

Thr Asn Ile Leu Ala Leu Asn Ala Ala Val Glu Ala Ala Arg Ala Gly
        115                 120                 125
```

Glu Gln Gly Arg Gly Phe Ala Val Val Ala Gly Val Arg Asn Leu
    130                 135                 140

Ala Gln Arg Ser Ala Gln Ala Ala Arg Glu Ile Lys Ser Leu Ile Glu
145                 150                 155                 160

Asp Ser Val Gly Lys Val Asp Val Gly Ser Thr Leu Val Glu Ser Ala
                165                 170                 175

Gly Glu Thr Met Ala Glu Ile Val Ser Ala Val Thr Arg Val Thr Asp
                180                 185                 190

Ile Met Gly Glu Ile Ala Ser Ala Ser Asp Glu Gln Ser Arg Gly Ile
            195                 200                 205

Asp Gln Val Gly Leu Ala Val Ala Glu Met Asp Arg Val Thr Gln Gln
    210                 215                 220

Asn Ala Ala Leu Val Glu Glu Ser Ala Ala Ala Ala Ala Leu Glu
225                 230                 235                 240

Glu Gln Ala Ser Arg Leu Thr Glu Ala Val Ala Val Phe Arg Ile Gln
                245                 250                 255

Gln Gln Gln Arg Glu Thr Ser Ala Val Val Lys Thr Val Thr Pro Ala
                260                 265                 270

Ala Pro

<210> SEQ ID NO 80
<211> LENGTH: 268
<212> TYPE: PRT
<213> ORGANISM: Halobacterium salinarum

<400> SEQUENCE: 80

Leu Glu Ala Thr Ser Gln Asp Val Ala Glu Arg Thr Asp Thr Met Arg
1               5                   10                  15

Ala Arg Thr Asp Asp Gln Val Asp Arg Met Ala Asp Val Ser Arg Glu
                20                  25                  30

Ile Ser Ser Val Ser Ala Ser Val Glu Glu Val Ala Ser Thr Ala Asp
            35                  40                  45

Asp Val Arg Arg Thr Ser Glu Asp Ala Glu Ala Leu Ala Gln Gln Gly
    50                  55                  60

Glu Ala Ala Asp Asp Ala Leu Ala Thr Met Thr Asp Ile Asp Glu
65                  70                  75                  80

Ala Thr Asp Gly Val Thr Ala Gly Val Glu Gln Leu Gly Glu Arg Ala
                85                  90                  95

Ala Asp Val Glu Ser Val Thr Gly Val Ile Asp Ile Ala Glu Gln
                100                 105                 110

Thr Asn Met Leu Ala Leu Asn Ala Ser Ile Glu Ala Ala Arg Ala Gly
            115                 120                 125

Glu Ala Gly Glu Gly Phe Ala Val Val Ala Asp Glu Val Lys Ala Leu
    130                 135                 140

Ala Glu Glu Ser Arg Glu Gln Ser Thr Arg Val Glu Glu Leu Val Glu
145                 150                 155                 160

Gln Met Gln Ala Glu Thr Glu Glu Thr Val Asp Gln Leu Asp Glu Val
                165                 170                 175

Asn Gln Arg Ile Gly Glu Gly Val Glu Arg Val Glu Glu Ala Met Glu
                180                 185                 190

Thr Leu Gln Glu Ile Thr Asp Ala Val Glu Asp Ala Ala Ser Gly Met
            195                 200                 205

Gln Glu Val Ser Thr Ala Thr Asp Glu Gln Ala Val Ser Thr Glu Glu
    210                 215                 220

```
Val Ala Glu Met Val Asp Gly Val Asp Arg Ala Gly Glu Ile Ala
225                 230                 235                 240

Ala Ala Leu Asp Asp Ile Ala Asp Ala Thr Asp Gln Gln Val Arg Thr
                245                 250                 255

Val Glu Glu Val Arg Glu Thr Val Gly Lys Leu Ser
            260                 265
```

<210> SEQ ID NO 81
<211> LENGTH: 235
<212> TYPE: PRT
<213> ORGANISM: Bacillus subtilis

<400> SEQUENCE: 81

```
Leu His Gln Lys Ile Gln Glu Thr Ser Gly Ser Ile Ala Asn Leu Phe
1               5                   10                  15

Ser Glu Thr Ser Arg Ser Val Gln Glu Leu Val Asp Lys Ser Glu Gly
                20                  25                  30

Ile Ser Gln Ala Ser Lys Ala Gly Thr Val Thr Ser Ser Thr Val Glu
            35                  40                  45

Glu Lys Ser Ile Gly Gly Lys Lys Glu Leu Glu Val Gln Gln Lys Gln
        50                  55                  60

Met Asn Lys Ile Asp Thr Ser Leu Val Gln Ile Glu Lys Glu Met Val
65                  70                  75                  80

Lys Leu Asp Glu Ile Ala Gln Gln Ile Glu Lys Ile Phe Gly Ile Val
                85                  90                  95

Thr Gly Ile Ala Glu Gln Thr Asn Leu Leu Ser Leu Asn Ala Ser Ile
            100                 105                 110

Glu Ser Ala Arg Ala Gly Glu His Gly Lys Gly Phe Ala Val Val Ala
        115                 120                 125

Asn Glu Val Arg Lys Leu Ser Glu Asp Thr Lys Lys Thr Val Ser Thr
130                 135                 140

Val Ser Glu Leu Val Asn Asn Thr Asn Thr Gln Ile Asn Ile Val Ser
145                 150                 155                 160

Lys His Ile Lys Asp Val Asn Glu Leu Val Ser Glu Ser Lys Glu Lys
                165                 170                 175

Met Thr Gln Ile Asn Arg Leu Phe Asp Glu Ile Val His Ser Met Lys
            180                 185                 190

Ile Ser Lys Glu Gln Ser Gly Lys Ile Asp Val Asp Leu Gln Ala Phe
        195                 200                 205

Leu Gly Gly Leu Gln Glu Val Ser Arg Ala Val Ser His Val Ala Ala
    210                 215                 220

Ser Val Asp Ser Leu Val Ile Leu Thr Glu Glu
225                 230                 235
```

<210> SEQ ID NO 82
<211> LENGTH: 27
<212> TYPE: PRT
<213> ORGANISM: Artificial Sequence
<220> FEATURE:
<223> OTHER INFORMATION: Description of Artificial Sequence: Myoglobin recognition sequence
<221> NAME/KEY: UNSURE
<222> LOCATION: (20)..(21)
<223> OTHER INFORMATION: Xaa at positions 11, 20 and 21 is unknown

```
<400> SEQUENCE: 82

Gly Gln Asp Val Leu Val Val Leu Ile Lys Xaa His Pro Leu Ile Gln
 1               5                  10                  15

Glu Lys Ile Xaa Xaa Phe Asp Phe Phe Lys His
            20                  25

<210> SEQ ID NO 83
<211> LENGTH: 21
<212> TYPE: PRT
<213> ORGANISM: Artificial Sequence
<220> FEATURE:
<223> OTHER INFORMATION: Description of Artificial Sequence: Myoglobin
      recognition sequence
<221> NAME/KEY: UNSURE
<222> LOCATION: (4)..(12)
<223> OTHER INFORMATION: Xaa at positions 4 and 12 is unknown

<400> SEQUENCE: 83

Ala Gln Arg Xaa Arg Leu Ala Gln Ile His Ala Xaa Lys Gly Lys Ile
 1               5                  10                  15

Pro Asp Trp Tyr Leu
            20

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Myoglobin
      recognition sequence
<221> NAME/KEY: UNSURE
<222> LOCATION: (4)..(15)
<223> OTHER INFORMATION: Xaa at positions 4, 10, 14 and 15 is unknown

<400> SEQUENCE: 84

Ile Ile Lys Xaa Thr Val Pro Val Leu Xaa Glu His Gly Xaa Xaa Ile
 1               5                  10                  15

<210> SEQ ID NO 85
<211> LENGTH: 24
<212> TYPE: PRT
<213> ORGANISM: Artificial Sequence
<220> FEATURE:
<223> OTHER INFORMATION: Description of Artificial Sequence: Myoglobin
      recognition sequence
<221> NAME/KEY: UNSURE
<222> LOCATION: (11)
<223> OTHER INFORMATION: Xaa at position 11 is unknown

<400> SEQUENCE: 85

Gly Gln Asp Val Leu Val Val Leu Ile Lys Xaa Asn Pro Glu Ile Gln
 1               5                  10                  15

Glu Lys Phe Phe Phe Phe Lys His
            20

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Myoglobin
      recognition sequence
<221> NAME/KEY: UNSURE
<222> LOCATION: (4)..(12)
<223> OTHER INFORMATION: Xaa at positions 4 and 12 is unknown
```

-continued

```
<400> SEQUENCE: 86

Ala Gln Arg Xaa Arg Leu Ala Gln Ile His Ala Xaa Lys Gly Lys Ile
 1               5                  10                  15

Pro Asp Trp Tyr Leu
             20
```